United States Patent
Fernandez et al.

(10) Patent No.: US 11,499,151 B2
(45) Date of Patent: Nov. 15, 2022

(54) METHODS AND SYSTEMS FOR ANALYZING GUIDE RNA MOLECULES

(71) Applicant: Editas Medicine, Inc., Cambridge, MA (US)

(72) Inventors: Cecilia Fernandez, Cambridge, MA (US); Georgia Giannoukos, Cambridge, MA (US); Luis Barrera, Cambridge, MA (US); Dawn Ciulla, Cambridge, MA (US); Terence Ta, Cambridge, MA (US)

(73) Assignee: Editas Medicine, Inc., Cambridge, MA (US)

( * ) Notice: Subject to any disclaimer, the term of this patent is extended or adjusted under 35 U.S.C. 154(b) by 325 days.

(21) Appl. No.: 16/608,411

(22) PCT Filed: Apr. 27, 2018

(86) PCT No.: PCT/US2018/030017
§ 371 (c)(1),
(2) Date: Oct. 25, 2019

(87) PCT Pub. No.: WO2018/201086
PCT Pub. Date: Nov. 1, 2018

(65) Prior Publication Data
US 2020/0190513 A1    Jun. 18, 2020

Related U.S. Application Data

(60) Provisional application No. 62/492,013, filed on Apr. 28, 2017.

(51) Int. Cl.
| C12N 15/113 | (2010.01) |
| C12Q 1/6827 | (2018.01) |
| C12Q 1/6876 | (2018.01) |

(52) U.S. Cl.
CPC .......... *C12N 15/113* (2013.01); *C12Q 1/6827* (2013.01); *C12Q 1/6876* (2013.01); *C12N 2310/20* (2017.05); *C12Q 2545/101* (2013.01)

(58) Field of Classification Search
CPC .......... C12N 15/113; C12N 2310/20; C12Q 1/6876; C12Q 1/6887; C12Q 2545/101
USPC ............. 435/6.1, 91.1, 91.31, 455, 458; 514/44 A, 44 R; 536/23.1, 24.5
See application file for complete search history.

(56) References Cited

U.S. PATENT DOCUMENTS

| 5,962,272 A | 10/1999 | Chenchik et al. |
| 8,546,553 B2 | 10/2013 | Terns et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,023,649 B2 | 5/2015 | Mali et al. |
| 9,074,199 B1 | 7/2015 | Chavez et al. |
| 9,234,213 B2 | 1/2016 | Wu |
| 9,260,723 B2 | 2/2016 | Mali et al. |
| 9,260,752 B1 | 2/2016 | May et al. |
| 9,267,135 B2 | 2/2016 | Church et al. |
| 9,322,037 B2 | 4/2016 | Liu et al. |
| 9,388,430 B2 | 7/2016 | Liu et al. |
| 9,404,098 B2 | 8/2016 | Terns et al. |
| 9,410,198 B2 | 8/2016 | May et al. |
| 9,422,553 B2 | 8/2016 | Terns et al. |
| 9,512,446 B1 | 12/2016 | Joung et al. |
| 9,567,603 B2 | 2/2017 | Joung et al. |
| 9,567,604 B2 | 2/2017 | Joung et al. |
| 9,587,252 B2 | 3/2017 | Church et al. |
| 9,637,739 B2 | 5/2017 | Siksnys et al. |
| 9,663,782 B2 | 5/2017 | Yu et al. |
| 9,688,971 B2 | 6/2017 | Doudna et al. |
| 9,725,714 B2 | 8/2017 | May et al. |
| 9,738,908 B2 | 8/2017 | Wu |
| 9,752,132 B2 | 9/2017 | Joung et al. |
| 9,790,490 B2 | 10/2017 | Zhang et al. |
| 9,803,194 B2 | 10/2017 | May et al. |
| 9,809,814 B1 | 11/2017 | May et al. |
| 9,822,370 B2 | 11/2017 | Musunuru et al. |
| 9,822,372 B2 | 11/2017 | Zhang et al. |
| 9,840,713 B2 | 12/2017 | Zhang |
| 9,873,894 B2 | 1/2018 | Conway et al. |
| 9,879,269 B2 | 1/2018 | Barrangou et al. |
| 9,885,026 B2 | 2/2018 | Brouns et al. |
| 9,902,974 B2 | 2/2018 | Conway et al. |
| 9,909,122 B2 | 3/2018 | May et al. |
| 9,926,545 B2 | 3/2018 | Joung et al. |
| 9,926,546 B2 | 3/2018 | Joung et al. |
| 9,944,912 B2 | 4/2018 | Joung et al. |
| 9,963,689 B2 | 5/2018 | Doudna et al. |
| 9,970,001 B2 | 5/2018 | Miller |
| 9,970,024 B2 | 5/2018 | Church et al. |

(Continued)

FOREIGN PATENT DOCUMENTS

| WO | WO-2007/025097 A2 | 3/2007 |
| WO | WO-2010/011961 A2 | 1/2010 |

(Continued)

OTHER PUBLICATIONS

US 10,077,445 B2, 09/2018, Dounda et al. (withdrawn)

(Continued)

*Primary Examiner* — Jane J Zara
(74) *Attorney, Agent, or Firm* — Charles E. Lyon; Rolando Medina; Margo R. Monroe

(57) ABSTRACT

The present disclosure relates to methods of assessing a sample of guide RNAs (gRNAs).

19 Claims, 18 Drawing Sheets

Specification includes a Sequence Listing.

(56) References Cited

U.S. PATENT DOCUMENTS

| | | |
|---|---|---|
| 10,066,233 B2 | 9/2018 | Barrangou et al. |
| 10,077,453 B2 | 9/2018 | Liu et al. |
| 10,093,910 B2 | 10/2018 | Joung et al. |
| 10,100,291 B2 | 10/2018 | Chavez et al. |
| 10,113,167 B2 | 10/2018 | Doudna et al. |
| 10,113,179 B2 | 10/2018 | Begemann et al. |
| 10,113,207 B2 | 10/2018 | Wang |
| 10,119,133 B2 | 11/2018 | Joung et al. |
| 10,125,361 B2 | 11/2018 | May et al. |
| 10,202,589 B2 | 2/2019 | Joung et al. |
| 10,202,619 B2 | 2/2019 | Wu |
| 10,227,611 B2 | 3/2019 | Doudna et al. |
| 10,266,850 B2 | 4/2019 | Doudna et al. |
| 10,301,651 B2 | 5/2019 | Doudna et al. |
| 10,308,961 B2 | 6/2019 | Doudna et al. |
| 10,329,587 B2 | 6/2019 | Church et al. |
| 10,351,878 B2 | 7/2019 | Doudna et al. |
| 10,358,658 B2 | 7/2019 | Doudna et al. |
| 10,358,659 B2 | 7/2019 | Doudna et al. |
| 10,377,998 B2 | 8/2019 | Zhang et al. |
| 10,378,027 B2 | 8/2019 | Joung et al. |
| 10,385,360 B2 | 8/2019 | Doudna et al. |
| 10,392,607 B2 | 8/2019 | Sternberg et al. |
| 10,400,253 B2 | 9/2019 | Doudna et al. |
| 10,407,697 B2 | 9/2019 | Doudna et al. |
| 10,415,059 B2 | 9/2019 | Joung et al. |
| 10,415,061 B2 | 9/2019 | Doudna et al. |
| 10,421,980 B2 | 9/2019 | Doudna et al. |
| 10,428,319 B2 | 10/2019 | Steinberg et al. |
| 10,428,352 B2 | 10/2019 | Doudna et al. |
| 10,435,679 B2 | 10/2019 | Chavez et al. |
| 10,435,708 B2 | 10/2019 | Mali et al. |
| 10,443,076 B2 | 10/2019 | Doudna et al. |
| 2010/0076057 A1 | 3/2010 | Sontheimer et al. |
| 2010/0093617 A1 | 4/2010 | Barrangou et al. |
| 2013/0011828 A1 | 1/2013 | Barrangou et al. |
| 2014/0068797 A1 | 3/2014 | Doudna et al. |
| 2014/0093941 A1 | 4/2014 | Terns et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0242664 A1 | 8/2014 | Zhang et al. |
| 2014/0242699 A1 | 8/2014 | Zhang |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273233 A1 | 9/2014 | Chen et al. |
| 2014/0287938 A1 | 9/2014 | Zhang et al. |
| 2014/0294773 A1 | 10/2014 | Brouns et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356956 A1 | 12/2014 | Church et al. |
| 2014/0357523 A1 | 12/2014 | Zeiner et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0071889 A1 | 3/2015 | Musunuru et al. |
| 2015/0071898 A1 | 3/2015 | Liu et al. |
| 2015/0071899 A1 | 3/2015 | Liu et al. |
| 2015/0079681 A1 | 3/2015 | Zhang |
| 2015/0176013 A1 | 6/2015 | Musunuru et al. |
| 2015/0184139 A1 | 7/2015 | Zhang et al. |
| 2015/0203872 A1 | 7/2015 | Zhang |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0259684 A1 | 9/2015 | Church et al. |
| 2015/0259704 A1 | 9/2015 | Church et al. |
| 2015/0284727 A1 | 10/2015 | Kim et al. |
| 2015/0291961 A1 | 10/2015 | Siksnys et al. |
| 2015/0291965 A1 | 10/2015 | Zhang et al. |
| 2015/0291966 A1 | 10/2015 | Zhang et al. |
| 2015/0322457 A1 | 11/2015 | Kim et al. |
| 2015/0344912 A1 | 12/2015 | Kim et al. |
| 2015/0353905 A1 | 12/2015 | Weiss et al. |
| 2015/0353917 A1 | 12/2015 | Miller |
| 2015/0356239 A1 | 12/2015 | Zhang et al. |
| 2016/0002670 A1 | 1/2016 | Church et al. |
| 2016/0010076 A1 | 1/2016 | Joung et al. |
| 2016/0010154 A1 | 1/2016 | Laganiere et al. |
| 2016/0017366 A1 | 1/2016 | Chen et al. |
| 2016/0024523 A1 | 1/2016 | Joung et al. |
| 2016/0024524 A1 | 1/2016 | Joung et al. |
| 2016/0032274 A1 | 2/2016 | Church et al. |
| 2016/0046949 A1 | 2/2016 | May et al. |
| 2016/0046961 A1 | 2/2016 | Jinek et al. |
| 2016/0046962 A1 | 2/2016 | May et al. |
| 2016/0046963 A1 | 2/2016 | May et al. |
| 2016/0046978 A1 | 2/2016 | May et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0068887 A1 | 3/2016 | May et al. |
| 2016/0076020 A1 | 3/2016 | May et al. |
| 2016/0090607 A1 | 3/2016 | Conway et al. |
| 2016/0102324 A1 | 4/2016 | Duchateau et al. |
| 2016/0108470 A1 | 4/2016 | May et al. |
| 2016/0115488 A1 | 4/2016 | Zhang et al. |
| 2016/0115489 A1 | 4/2016 | Zhang et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153006 A1 | 6/2016 | Zhang et al. |
| 2016/0160210 A1 | 6/2016 | Mali et al. |
| 2016/0168592 A1 | 6/2016 | Church et al. |
| 2016/0175462 A1 | 6/2016 | Zhang et al. |
| 2016/0184362 A1 | 6/2016 | Duchateau et al. |
| 2016/0186152 A1 | 6/2016 | Brouns et al. |
| 2016/0186213 A1 | 6/2016 | Zhang et al. |
| 2016/0186214 A1 | 6/2016 | Brouns et al. |
| 2016/0201089 A1 | 7/2016 | Gersbach et al. |
| 2016/0208243 A1 | 7/2016 | Zhang et al. |
| 2016/0215276 A1 | 7/2016 | Liu et al. |
| 2016/0222416 A1 | 8/2016 | Church et al. |
| 2016/0237455 A1 | 8/2016 | Glucksmann et al. |
| 2016/0237456 A1 | 8/2016 | Church et al. |
| 2016/0251640 A1 | 9/2016 | May et al. |
| 2016/0272965 A1 | 9/2016 | Zhang et al. |
| 2016/0281072 A1 | 9/2016 | Zhang |
| 2016/0298097 A1 | 10/2016 | Chavez et al. |
| 2016/0298125 A1 | 10/2016 | Chen et al. |
| 2016/0298132 A1 | 10/2016 | Chen et al. |
| 2016/0298133 A1 | 10/2016 | Chen et al. |
| 2016/0298134 A1 | 10/2016 | Chen et al. |
| 2016/0298135 A1 | 10/2016 | Chen et al. |
| 2016/0298136 A1 | 10/2016 | Chen et al. |
| 2016/0298137 A1 | 10/2016 | Chen et al. |
| 2016/0298138 A1 | 10/2016 | Chen et al. |
| 2016/0304907 A1 | 10/2016 | Mali et al. |
| 2016/0312198 A1 | 10/2016 | Joung et al. |
| 2016/0312199 A1 | 10/2016 | Joung et al. |

(56) References Cited

U.S. PATENT DOCUMENTS

| | | |
|---|---|---|
| 2016/0312280 A1 | 10/2016 | May et al. |
| 2016/0319260 A1 | 11/2016 | Joung et al. |
| 2016/0319261 A1 | 11/2016 | Joung et al. |
| 2016/0319281 A1 | 11/2016 | Tsai et al. |
| 2016/0319349 A1 | 11/2016 | May et al. |
| 2016/0340662 A1 | 11/2016 | Zhang et al. |
| 2016/0355796 A1 | 12/2016 | Davidson et al. |
| 2016/0355797 A1 | 12/2016 | Konermann et al. |
| 2016/0355816 A1 | 12/2016 | Terns et al. |
| 2017/0037416 A1 | 2/2017 | Barrangou et al. |
| 2017/0044569 A9 | 2/2017 | Church et al. |
| 2017/0051276 A1 | 2/2017 | May et al. |
| 2017/0051310 A1 | 2/2017 | Doudna et al. |
| 2017/0051312 A1 | 2/2017 | Jinek et al. |
| 2017/0058271 A1 | 3/2017 | Joung et al. |
| 2017/0073705 A1 | 3/2017 | Chen et al. |
| 2017/0081650 A1 | 3/2017 | Joung et al. |
| 2017/0107536 A1 | 4/2017 | Zhang et al. |
| 2017/0114369 A1 | 4/2017 | Donohoue et al. |
| 2017/0152508 A1 | 6/2017 | Joung et al. |
| 2017/0152528 A1 | 6/2017 | Zhang |
| 2017/0166893 A1 | 6/2017 | Doudna et al. |
| 2017/0166903 A1 | 6/2017 | Zhang et al. |
| 2017/0175142 A1 | 6/2017 | Zhang et al. |
| 2017/0175144 A1 | 6/2017 | Zhang et al. |
| 2017/0191078 A1 | 7/2017 | Zhang et al. |
| 2017/0191082 A1 | 7/2017 | Chen et al. |
| 2017/0198269 A1 | 7/2017 | Zhang et al. |
| 2017/0211142 A1 | 7/2017 | Smargon et al. |
| 2017/0233703 A1 | 8/2017 | Xie et al. |
| 2017/0268022 A1 | 9/2017 | Liu et al. |
| 2017/0298330 A1 | 10/2017 | Sato et al. |
| 2017/0306307 A1 | 10/2017 | Zhang et al. |
| 2017/0306335 A1 | 10/2017 | Zhang et al. |
| 2017/0327805 A1 | 11/2017 | Joung et al. |
| 2017/0327806 A1 | 11/2017 | Joung et al. |
| 2017/0327820 A1 | 11/2017 | May et al. |
| 2017/0349915 A1 | 12/2017 | May et al. |
| 2018/0002682 A1 | 1/2018 | Sternberg et al. |
| 2018/0030425 A1 | 2/2018 | Joung et al. |
| 2018/0066242 A1 | 3/2018 | Zhang et al. |
| 2018/0073002 A1 | 3/2018 | Deiters et al. |
| 2018/0080051 A1 | 3/2018 | Sheikh et al. |
| 2018/0100147 A1 | 4/2018 | Yates et al. |
| 2018/0100148 A1 | 4/2018 | Vakulskas et al. |
| 2018/0119121 A1 | 5/2018 | Brouns et al. |
| 2018/0119175 A1 | 5/2018 | Conway et al. |
| 2018/0127780 A1 | 5/2018 | Liu et al. |
| 2018/0135073 A1 | 5/2018 | Chen et al. |
| 2018/0148735 A1 | 5/2018 | Begemann et al. |
| 2018/0155708 A1 | 6/2018 | Church et al. |
| 2018/0155716 A1 | 6/2018 | Zhang et al. |
| 2018/0163188 A1 | 6/2018 | Xie et al. |
| 2018/0163213 A1 | 6/2018 | Aneja et al. |
| 2018/0187176 A1 | 7/2018 | Behlke et al. |
| 2018/0187195 A1 | 7/2018 | Siksnys et al. |
| 2018/0208931 A1 | 7/2018 | Doudna et al. |
| 2018/0216088 A1 | 8/2018 | Joung et al. |
| 2018/0230495 A1 | 8/2018 | Doudna et al. |
| 2018/0230496 A1 | 8/2018 | Doudna et al. |
| 2018/0230497 A1 | 8/2018 | Doudna et al. |
| 2018/0237801 A1 | 8/2018 | Doudna et al. |
| 2018/0245100 A1 | 8/2018 | Doudna et al. |
| 2018/0245101 A1 | 8/2018 | Doudna et al. |
| 2018/0251788 A1 | 9/2018 | Donohoue et al. |
| 2018/0251791 A1 | 9/2018 | Doudna et al. |
| 2018/0251793 A1 | 9/2018 | Doudna et al. |
| 2018/0251794 A1 | 9/2018 | Doudna et al. |
| 2018/0251795 A1 | 9/2018 | Charpentier et al. |
| 2018/0265864 A1 | 9/2018 | Li et al. |
| 2018/0273981 A1 | 9/2018 | Doudna et al. |
| 2018/0282713 A1 | 10/2018 | Van Der Oost |
| 2018/0282714 A1 | 10/2018 | Joung et al. |
| 2018/0282764 A1 | 10/2018 | Jinek et al. |
| 2018/0291383 A1 | 10/2018 | Musunuru et al. |
| 2018/0298360 A1 | 10/2018 | Sternberg et al. |
| 2018/0298406 A1 | 10/2018 | Doudna et al. |
| 2018/0298407 A1 | 10/2018 | Doudna et al. |
| 2018/0312824 A1 | 11/2018 | Zhang et al. |
| 2018/0312874 A1 | 11/2018 | Doudna et al. |
| 2018/0312875 A1 | 11/2018 | Doudna et al. |
| 2018/0312876 A1 | 11/2018 | Doudna et al. |
| 2018/0320163 A1 | 11/2018 | Koonin et al. |
| 2018/0320197 A1 | 11/2018 | Gersbach et al. |
| 2018/0320201 A1 | 11/2018 | Vakulskas et al. |
| 2018/0327761 A1 | 11/2018 | Duchateau et al. |
| 2018/0346927 A1 | 12/2018 | Doudna et al. |
| 2018/0355332 A1 | 12/2018 | Steinberg et al. |
| 2019/0002889 A1 | 1/2019 | Cheng et al. |
| 2019/0002921 A1 | 1/2019 | Doudna et al. |
| 2019/0002922 A1 | 1/2019 | Doudna et al. |
| 2019/0002923 A1 | 1/2019 | Doudna et al. |
| 2019/0010471 A1 | 1/2019 | Zhang et al. |
| 2019/0010481 A1 | 1/2019 | Joung et al. |
| 2019/0010520 A1 | 1/2019 | Doudna et al. |
| 2019/0048340 A1 | 2/2019 | Charpentier et al. |
| 2019/0062790 A1 | 2/2019 | Doudna et al. |
| 2019/0071688 A1 | 3/2019 | Begemann et al. |
| 2019/0083656 A1 | 3/2019 | Khalili et al. |
| 2019/0085329 A1 | 3/2019 | Siksnys et al. |
| 2019/0093129 A1 | 3/2019 | Doudna et al. |
| 2019/0106687 A1 | 4/2019 | Joung et al. |
| 2019/0106711 A1 | 4/2019 | Doudna et al. |
| 2019/0106712 A1 | 4/2019 | Doudna et al. |
| 2019/0106713 A1 | 4/2019 | Doudna et al. |
| 2019/0106714 A1 | 4/2019 | Doudna et al. |
| 2019/0106715 A1 | 4/2019 | Doudna et al. |
| 2019/0218602 A1 | 7/2019 | Zhang et al. |
| 2019/0264186 A1 | 8/2019 | Yamano et al. |
| 2019/0284583 A1 | 9/2019 | Doudna et al. |

FOREIGN PATENT DOCUMENTS

| | | |
|---|---|---|
| WO | WO-2013/098244 A1 | 7/2013 |
| WO | WO-2013/141680 A1 | 9/2013 |
| WO | WO-2013/142578 A1 | 9/2013 |
| WO | WO-2013/176772 A1 | 11/2013 |
| WO | WO-2014/018423 A2 | 1/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/145599 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/186585 A2 | 11/2014 |
| WO | WO-2014/191518 A1 | 12/2014 |
| WO | WO-2014/191521 A2 | 12/2014 |
| WO | WO-2014/197568 A2 | 12/2014 |
| WO | WO-2014/197748 A2 | 12/2014 |
| WO | WO-2014/204578 A1 | 12/2014 |
| WO | WO-2014/204724 A1 | 12/2014 |
| WO | WO-2014/204725 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006290 A1 | 1/2015 |
| WO | WO-2015/006294 A2 | 1/2015 |

(56) References Cited

FOREIGN PATENT DOCUMENTS

| | | |
|---|---|---|
| WO | WO-2015/010114 A1 | 1/2015 |
| WO | WO-2015/013583 A2 | 1/2015 |
| WO | WO-2015/021426 A1 | 2/2015 |
| WO | WO-2015/035162 A2 | 3/2015 |
| WO | WO-2015/048577 A2 | 4/2015 |
| WO | WO-2015/070083 A1 | 5/2015 |
| WO | WO-2015/077318 A1 | 5/2015 |
| WO | WO-2015/089351 A1 | 6/2015 |
| WO | WO-2015/089354 A1 | 6/2015 |
| WO | WO-2015/089427 A1 | 6/2015 |
| WO | WO-2015/089486 A2 | 6/2015 |
| WO | WO-2015/094861 A1 | 6/2015 |
| WO | WO-2015/138510 A1 | 9/2015 |
| WO | WO-2015/188056 A1 | 12/2015 |
| WO | WO-2015/188065 A1 | 12/2015 |
| WO | WO-2016/022363 A2 | 2/2016 |
| WO | WO-2016/028682 A1 | 2/2016 |
| WO | WO-2016/057821 A2 | 4/2016 |
| WO | WO-2016/057951 A2 | 4/2016 |
| WO | WO-2016057951 A2 * | 4/2016 ........... C12N 15/102 |
| WO | WO-2016/073990 A2 | 5/2016 |
| WO | WO-2016/081923 A2 | 5/2016 |
| WO | WO-2016/094867 A1 | 6/2016 |
| WO | WO-2016/106236 A1 | 6/2016 |
| WO | WO-2016/106244 A1 | 6/2016 |
| WO | WO-2016094867 A1 * | 6/2016 ......... A01K 67/0275 |
| WO | WO-2016/112242 A1 | 7/2016 |
| WO | WO-2016/114972 A1 | 7/2016 |
| WO | WO-2016/141224 A1 | 9/2016 |
| WO | WO-2016/161207 A1 | 10/2016 |
| WO | WO-2016/164797 A1 | 10/2016 |
| WO | WO-2016/166340 A1 | 10/2016 |
| WO | WO-2016/167300 A1 | 10/2016 |
| WO | WO-2016/196655 A1 | 12/2016 |
| WO | WO-2016/205613 A1 | 12/2016 |
| WO | WO-2016/205711 A1 | 12/2016 |
| WO | WO-2016/205749 A1 | 12/2016 |
| WO | WO-2016/205759 A1 | 12/2016 |
| WO | WO-2017/015015 A1 | 1/2017 |
| WO | WO-2017/040348 A1 | 3/2017 |
| WO | WO-2017/048969 A1 | 3/2017 |
| WO | WO-2017/048993 A1 | 3/2017 |
| WO | WO-2017/064546 A1 | 4/2017 |
| WO | WO-2017/066588 A2 | 4/2017 |
| WO | WO-2017/070633 A2 | 4/2017 |
| WO | WO-2017/099494 A1 | 6/2017 |
| WO | WO-2017/127807 A1 | 7/2017 |
| WO | WO-2017/136335 A1 | 8/2017 |
| WO | WO-2017/161068 A1 | 9/2017 |
| WO | WO-2017/181107 A2 | 10/2017 |
| WO | WO-2017/184768 A1 | 10/2017 |
| WO | WO-2017/189308 A1 | 11/2017 |
| WO | WO-2017/197238 A1 | 11/2017 |
| WO | WO-2017/216392 A1 | 12/2017 |
| WO | WO-2017/219027 A1 | 12/2017 |
| WO | WO-2017/219033 A1 | 12/2017 |
| WO | WO-2017/222773 A1 | 12/2017 |
| WO | WO-2018/022634 A1 | 2/2018 |
| WO | WO-2018/035387 A1 | 2/2018 |
| WO | WO-2018/035388 A1 | 2/2018 |
| WO | WO-2018/038772 A1 | 3/2018 |
| WO | WO-2018/049073 A1 | 3/2018 |
| WO | WO-2018/049077 A1 | 3/2018 |
| WO | WO-2018/049079 A1 | 3/2018 |
| WO | WO-2018/051347 A1 | 3/2018 |
| WO | WO-2018/052247 A1 | 3/2018 |
| WO | WO-2018/053053 A1 | 3/2018 |
| WO | WO-2018/064352 A1 | 4/2018 |
| WO | WO-2018/064371 A1 | 4/2018 |
| WO | WO-2018/068053 A2 | 4/2018 |
| WO | WO-2018/069474 A1 | 4/2018 |
| WO | WO-2018/071868 A1 | 4/2018 |
| WO | WO-2018/071892 A1 | 4/2018 |
| WO | WO-2018/074979 A1 | 4/2018 |
| WO | WO-2018/089664 A1 | 5/2018 |
| WO | WO-2018/098383 A1 | 5/2018 |
| WO | WO-2018/108272 A1 | 6/2018 |
| WO | WO-2018/108338 A1 | 6/2018 |
| WO | WO-2018/108339 A1 | 6/2018 |
| WO | WO-2018/109101 A1 | 6/2018 |
| WO | WO-2018/112451 A1 | 6/2018 |
| WO | WO-2018/126176 A1 | 7/2018 |
| WO | WO-2018/149888 A1 | 8/2018 |
| WO | WO-2018/170015 A1 | 9/2018 |
| WO | WO-2018/172556 A1 | 9/2018 |
| WO | WO-2018/183766 A1 | 10/2018 |
| WO | WO-2018/188571 A1 | 10/2018 |
| WO | WO-2018/191715 A2 | 10/2018 |
| WO | WO-2018/195540 A1 | 10/2018 |
| WO | WO-2018/195545 A2 | 10/2018 |
| WO | WO-2018/197495 A1 | 11/2018 |
| WO | WO-2018/201086 A1 | 11/2018 |
| WO | WO-2018/209712 A1 | 11/2018 |
| WO | WO-2018/213351 A1 | 11/2018 |
| WO | WO-2018/221685 A1 | 12/2018 |
| WO | WO-2018/226855 A1 | 12/2018 |
| WO | WO-2018/227114 A1 | 12/2018 |
| WO | WO-2019/006471 A2 | 1/2019 |
| WO | WO-2019/009682 A2 | 1/2019 |
| WO | WO-2019/018041 A1 | 1/2019 |
| WO | WO-2019/036513 A1 | 2/2019 |
| WO | WO-2019/040650 A1 | 2/2019 |
| WO | WO-2019/046540 A1 | 3/2019 |
| WO | WO-2019/049913 A1 | 3/2019 |
| WO | WO-2019/051419 A1 | 3/2019 |
| WO | WO-2019/060469 A2 | 3/2019 |
| WO | WO-2019/067322 A1 | 4/2019 |
| WO | WO-2019/072596 A1 | 4/2019 |
| WO | WO-2019/074542 A1 | 4/2019 |
| WO | WO-2019/089796 A1 | 5/2019 |
| WO | WO-2019/089804 A1 | 5/2019 |
| WO | WO-2019/089808 A1 | 5/2019 |
| WO | WO-2019/089820 A1 | 5/2019 |
| WO | WO-2019/090173 A1 | 5/2019 |
| WO | WO-2019/090174 A1 | 5/2019 |
| WO | WO-2019/090175 A1 | 5/2019 |
| WO | WO-2019/092042 A1 | 5/2019 |
| WO | WO-2019/099943 A1 | 5/2019 |
| WO | WO-2019/126709 A1 | 6/2019 |
| WO | WO-2019/126716 A1 | 6/2019 |
| WO | WO-2019/126762 A2 | 6/2019 |
| WO | WO-2019/126774 A1 | 6/2019 |
| WO | WO-2019/168953 A1 | 9/2019 |
| WO | WO-2019/178427 A1 | 9/2019 |
| WO | WO-2019/178428 A1 | 9/2019 |
| WO | WO-2019/183150 A1 | 9/2019 |

OTHER PUBLICATIONS

Quinn et al (Poster 336, Clontech Laboratories, A Streamlined Method for the Production, Screening, and Application of sgRNAs for CRISPR/Cas Gene Editing, (2014)) (Year: 2014).*
Xiao et al (Bioinformatics, vol. 30, No. 8, pp. 1180-1182 (2014)) (Year: 2014).*
Bae et al (Bioinformatics, vol. 30, No. 10, pp. 1473-1475 (2014)) (Year: 2014).*
Anders, C. et al., Structural basis of PAM-dependent target DNA recognition by the Cas9 endonuclease, Nature, 513(7519):569-73 (2014).
Bae, S. et al, Cas-OFFinder: a fast and versatile algorithm that searches for potential off-target sites of Cas9 RNA-guided endonucleases, Bioinformatics, 30: 1473-5 (2014).
Briner, A. E. et al. Guide RNA functional modules direct Cas9 activity and orthogonality Molecular Cell, 56(2), 333-339 (2014).
Davis, L. and Maizels, N., Homology-directed repair of DNA nicks via pathways distinct from canonical double-strand break repair, PNAS, 111(10): E924-E932 (2014).
Doench, J.G. et al, Optimized sgRNA design to maximize activity and minimize off-target effects of CRISPR-Cas9, Nat. Biotechnol., 34: 184-91 (2016).
Esvelt, K. M. and Wang, H.H., Genome-scale engineering for systems and synthetic biology, Molecular Systems Biology, 9:641, 1-17(2013).

(56) References Cited

OTHER PUBLICATIONS

Frit, P. et al, Alternative end-joining pathway(s): bricolage at DNA breaks, DNA Repair (Amst.). 17: 81-97 (2014).
Fu, Y. et al, Improving CRISPR-Cas nuclease specificity using truncated guide RNAs, Nat. Biotechnol., 32(3): 279-284 (2014).
Heigwer, F. et al., E-CRISP: fast CRISPR target site identification, Nat. methods, 11(2): 122-3 (2014).
Hsu, P.D. et al., DNA targeting specificity of RNA-guided Cas9 nucleases, Nat Biotechnol, 31(9): 827-832 (2013).
International Search Report for PCT/US2018/030017 (Methods and Systems for Analyzing Guide RNA Molecules, filed Apr. 27, 2018), issued by ISA/EPO, 6 pages (Jul. 30, 2018).
Iyama, T. and Wilson, D.M., DNA repair mechanisms in dividing and non-dividing cells, DNA Repair (Amst)., 12(8): 620-36 (2013).
Jiang, W. et al. RNA-guided editing of bacterial genomes using CRISPR-Cas systems, Nat Biotechnol., 31(3): 233-239 (2013).
Jinek, M. et al., A programmable dual-RNA-guided DNA endonuclease in adaptive, bacterial immunity, Science, 337(6096): 816-821 (2012).
Jinek, M. et al., Structures of Cas9 endonucleases reveal RNA-mediated conformational activation, Science, 343(6176), 1247997 (2014).
Komor, A. C. et al, Programmable editing of a target base in genomic DNA without double-stranded DNA cleavage, Nature, 533(7603): 420-424 (2016).
Makarova, K. S. et al, Evolution and classification of the CRISPR-Cas systems, Nat. Rev. Microbiol., 9(6): 467-77 (2011).
Mali, P. et al., RNA-guided human genome engineering via Cas9, Science, 339(6121): 823-826 (2013).
Nishimasu, H. et al., Crystal structure of Cas9 in complex with guide RNA and target DNA. Cell, 156: 935-949 (2014).
Nishimasu, H. et al., Crystal Structure of *Staphylococcus aureus* Cas9, Cell, 162:1113-1126 (2015).
Quinn, T. et al, A Streamline method for the production, screening, and application of sgRNAs for SRISPR/Cas gene editing, (Jan. 1, 2014), XP055236569, Retrieved from the Internet <<http://info.clontech.com/rs/clontech/images/633702 Guide It PS 0514 web.pdf>>. (Accessed on Dec. 15, 2015).
Ran, F.A. et al, Double nicking by RNA-guided CRISPR Cas9 for enhanced genome editing specificity, Cell, 154(6): 1380-9 (2013).
Shishkin, A. A., et al, Simultaneous generation of many RNA-seq libraries in a single reaction, Nat. Methods, 12(4): 323-325 (2015).
Shmakov, S. et al., Discovery and Functional Characterization of Diverse Class 2 CRISPR-Cas Systems, Molecular Cell, 60: 385-397 (2015).
Turchinovich, A. et al, Capture and Amplification by Tailing and Switching (CATS). An ultrasensitive ligation-independent method for generation of DNA libraries for deep sequencing from picogram amounts of DNA and RNA, RNA Biology, Landes Bioscience, US, 11(7):817-828 (2014).
Written Opinion for PCT/US2018/030017 (Methods and Systems for Analyzing Guide RNA Molecules, filed Apr. 27, 2018), issued by ISA/EPO, 9 pages (dated Jul. 30, 2018).
Xiao, A. et al, CasOT: a genome-wide Cas9/gRNA off-target searching tool, Bioinformatics, 30(8): 1180-1182 (2014).
Yamano, T. et al. Crystal Structure of Cpf1 in Complex with Guide RNA and Target DNA, Cell, 165(4): 949-962 (2016).
Zetsche et al., Cpf1 is a single RNA-guided endonuclease of a class 2 CRISPR-Cas system, Cell 163, 759-771 (2015).

\* cited by examiner

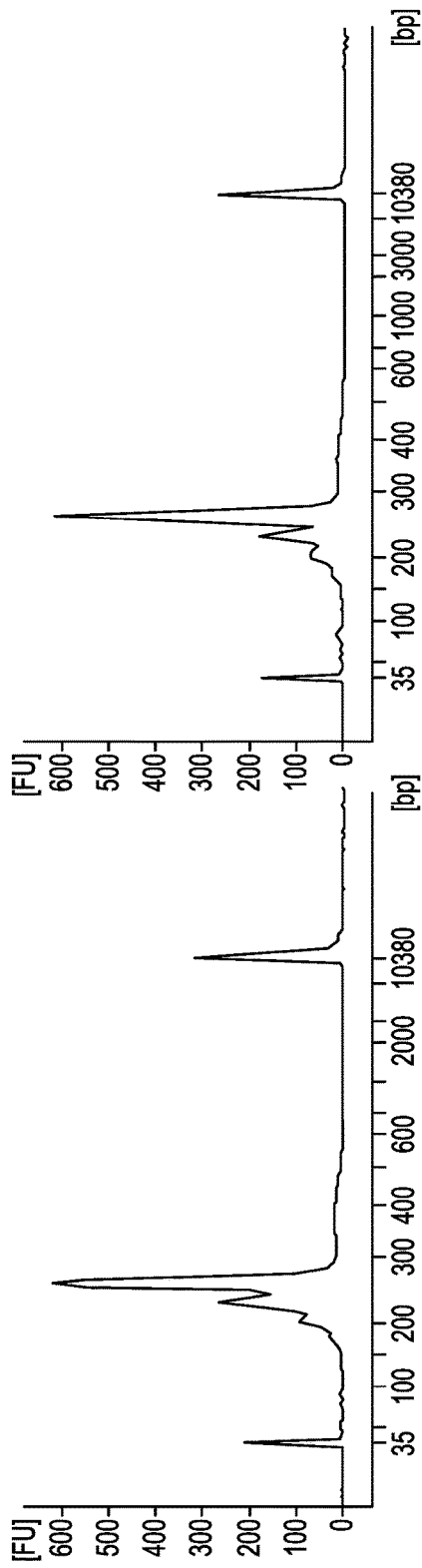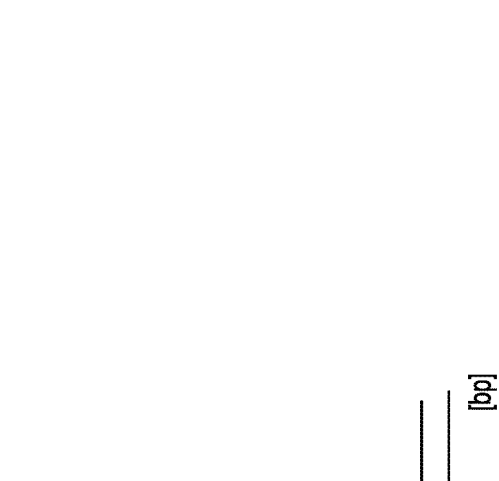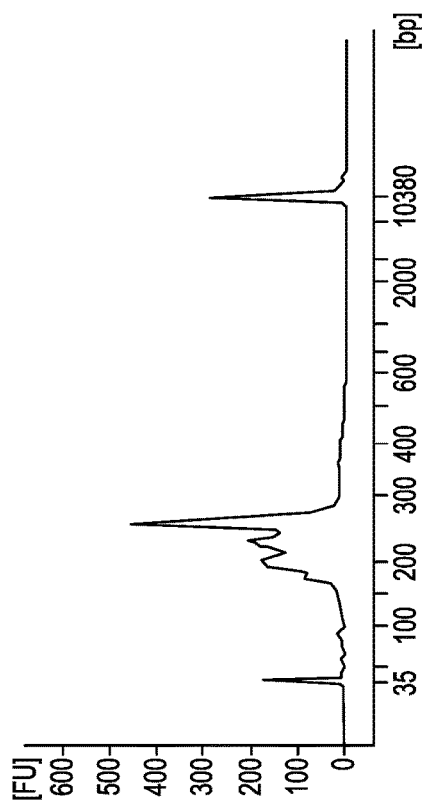
FIG. 2A
FIG. 2B
FIG. 2C

| Vendor | Format | ID | 5' End | 3' End | % Perfect_20 |
|---|---|---|---|---|---|
| A | sgRNA | A1 | | | 88.59 |
| | | A2 | | | 92.54 |
| | | A3 | | | 92.34 |
| | | A4 | | | 92.39 |
| | | A5 | | | 92.22 |
| | | A6 | | | 87.67 |
| | | A7 | | | 86.70 |
| | | A8 | | | 85.94 |
| | | A9 | | | 84.69 |
| | | A10 | | | 83.42 |
| | | A11 | | | 81.89 |
| B | sgRNA | B1 | | | 84.35 |
| C | sgRNA | C1 | | | 82.47 |
| | | C2 | | | 83.70 |
| | | C3 | | | 82.90 |
| | | C4 | | | 79.19 |
| | | C5 | | | 77.07 |
| | | C6 | | | 87.42 |
| | | C7 | | | 84.58 |
| | | C8 | | | 84.68 |
| | | C9 | | | 84.74 |
| | | C10 | | | 84.83 |
| | | C11 | | | 84.29 |
| | | C12 | | | 84.33 |
| | | C13 | 2'OMe/PS | 2'OMe/PS | 84.32 |
| | | C14 | 2'OMe/PS | 2'OMe/PS | 84.69 |
| | | C15 | | | 84.74 |
| | | C16 | | | 79.24 |
| | | C17 | 2'OMe/PS | 20XpolyA | 74.17 |
| D | sgRNA | D1 | | | 86.56 |
| | | D2 | | | 86.11 |
| | | D3 | | | 85.59 |
| | | D4 | | | 83.14 |
| | | D5 | | | 89.40 |
| | | D6 | | | 88.98 |
| | | D7 | | | 87.77 |
| E | IVT | E1 | ARCA | 20XpolyA | 96.26 |
| | | E2 | | 20XpolyA | 96.08 |
| | Proprietary | E3 | | | 95.73 |
| | | E4 | | | 96.77 |
| | | E5 | | | 95.07 |
| | | E6 | | | 95.16 |
| | | E7 | | | 95.87 |
| | | E8 | | 20XpolyA | 95.46 |
| | | E9 | InvG | | 96.61 |
| | | E10 | InvG | 20XpolyA | 96.63 |

% Perfect_20

70.00    98.00

SEQUENCE LISTING

```
<160> NUMBER OF SEQ ID NOS: 15

<210> SEQ ID NO 1
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(10)
<223> OTHER INFORMATION: /note="This sequence may encompass 1-10
      nucleotides"
<220> FEATURE:
<221> NAME/KEY: source
<223> OTHER INFORMATION: /note="See specification as filed for detailed
      description of substitutions and preferred embodiments"

<400> SEQUENCE: 1
aaaaaaaaaa                                                          10

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="This sequence may encompass 10-20
      nucleotides"
<220> FEATURE:
<221> NAME/KEY: source
<223> OTHER INFORMATION: /note="See specification as filed for detailed
      description of substitutions and preferred embodiments"

<400> SEQUENCE: 2
aaaaaaaaaa aaaaaaaaaa                                               20

<210> SEQ ID NO 3
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

```
<220> FEATURE:
<221> NAME/KEY: misc_feature
<222> LOCATION: (1)..(200)
<223> OTHER INFORMATION: /note="This sequence may encompass 25-200
      nucleotides"
<220> FEATURE:
<221> NAME/KEY: source
<223> OTHER INFORMATION: /note="See specification as filed for detailed
      description of substitutions and preferred embodiments"

<400> SEQUENCE: 3
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa                                                  200

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
aatgatacgg cgaccaccga                                                   20

<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
caagcagaag acggcatacg agat                                              24

<210> SEQ ID NO 6
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
acactctttc cctacacgac gctcttccga tct                                    33

<210> SEQ ID NO 7
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gtgactggag ttcagacgtg tgctcttccg atct                                   34

<210> SEQ ID NO 8
<211> LENGTH: 30
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
ccatctcatc cctgcgtgtc tccgactcag                                        30

<210> SEQ ID NO 9
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
cctctctatg ggcagtcggt gat                                               23

<210> SEQ ID NO 10
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (26)..(32)
<223> OTHER INFORMATION: a, c, t, u, g, unknown or other

<400> SEQUENCE: 10
cgcctacacg acgctcttcc gatctnnnnn nngcatggg                              39

<210> SEQ ID NO 11
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (35)..(44)
<223> OTHER INFORMATION: a, c, t, g, unknown or other

<400> SEQUENCE: 11
gtgactggag ttcagacgtg tgctcttccg atctnnnnnn nnnntcagtt tttcaagttg       60
ataacggtc                                                               69

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
```
aaaaaaaaaa aaaaaaaaaa                                                          20

<210> SEQ ID NO 13
<211> LENGTH: 100
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
ggggccacua gggacaggau guuuuagagc uagaaauagc aaguuaaaau aaggcuaguc    60
cguuaucaac uugaaaaagu ggcaccgagu cggugcuuuu                        100

<210> SEQ ID NO 14
<211> LENGTH: 81
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(52)
<223> OTHER INFORMATION: a, c, u, g, unknown or other
<220> FEATURE:
<221> NAME/KEY: modified_base
<222> LOCATION: (62)..(81)
<223> OTHER INFORMATION: a, c, u, g, unknown or other

<400> SEQUENCE: 14
nnnnnnnnnn nnnnnnnnnn nnnnnnnnnn nnnnnnnnnn nnnnnnnnnn nnggcuaguc    60
unnnnnnnnn nnnnnnnnnn n                                              81

<210> SEQ ID NO 15
<211> LENGTH: 81
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(52)
<223> OTHER INFORMATION: a, c, u, g, unknown or other
<220> FEATURE:
<221> NAME/KEY: modified_base
<222> LOCATION: (62)..(81)
<223> OTHER INFORMATION: a, c, u, g, unknown or other

<400> SEQUENCE: 15
nnnnnnnnnn nnnnnnnnnn nnnnnnnnnn nnnnnnnnnn nnnnnnnnnn nnggcuaguc    60
cnnnnnnnnn nnnnnnnnnn n                                              81

METHODS AND SYSTEMS FOR ANALYZING GUIDE RNA MOLECULES

CROSS-REFERENCE TO RELATED APPLICATION

This application claims the benefit of U.S. Provisional Application No. 62/492,013, filed Apr. 28, 2017, the contents of which are hereby incorporated by reference in their entirety.

FIELD

The present disclosure relates to methods of assessing a sample of guide RNAs (gRNAs).

BACKGROUND

CRISPRs (Clustered Regularly Interspaced Short Palindromic Repeats) evolved in bacteria and archaea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of an RNA-guided nuclease protein such as Cas9 or Cpf1 to a target sequence in the viral genome. The RNA-guided nuclease, in turn, cleaves and thereby silences the viral target.

CRISPR systems have been adapted for genome editing in eukaryotic cells. These systems generally include a protein component (the RNA-guided nuclease) and a nucleic acid component (generally referred to as a guide RNA or "gRNA"). These two components form a complex that interacts with specific target DNA sequences recognized by, or complementary to, the two components of the system and optionally edits or alters the target sequence, for example by means of site-specific DNA cleavage.

Guide RNA (gRNA) targeting sequences can govern on- and off-target genome editing activity of CRISPR systems. Current methods for assessing a sample of gRNAs include mass spectrometry methods that rely on mass information from predetermined gRNA sequences. However, such techniques can fail to identify presence of contaminants, such as nucleotide substitutions, insertions, or deletions, in a sample of gRNAs, which may cause off-target effects and hinder clinical applications.

SUMMARY

The present disclosure provides, among other things, methods and systems for assessing a sample of gRNA molecules. The disclosed systems and methods provide the ability to assess and/or validate sequence integrity of a sample of gRNAs.

In one aspect, the present disclosure provides methods for analyzing a guide RNA (gRNA) composition, comprising: generating a library of double-stranded complementary DNA (ds-cDNA) molecules, wherein (a) each of a plurality of ds-cDNA molecules in the library comprises (i) a first strand that is complementary to one of a plurality of gRNAs in the composition and (ii) a second strand that is complementary to the first strand, and (b) each of the first strands of the plurality of the ds-cDNA molecules includes a 3' sequence that is complementary to a 5' terminus of one of the plurality of gRNAs in the composition; sequencing the plurality of ds-cDNA molecules, thereby generating a plurality of sequence reads; and aligning each of the plurality of sequence reads to a reference sequence.

In some embodiments, the method further comprises the step of determining (e.g., measuring) a level (e.g., a fraction) of sequence reads comprising a truncation, insertion, deletion or substitution relative to the reference sequence, and optionally assigning a value to the gRNA composition based on the measured fraction of sequence reads. In some embodiments, the step of generating the library of ds-cDNA molecules includes contacting the gRNA composition with a reverse transcriptase, thereby generating a plurality of first strands of the ds-cDNA, and each first strand optionally comprises (a) a sequence that is complementary to the 5' terminus of one of the plurality of gRNAs in the composition, and (b) at least one nucleotide 3' of the sequence that is added by the reverse transcriptase.

In some embodiments, the step of generating the library of ds-cDNA molecules includes contacting one of the gRNA composition and a plurality of first strands with a ligase and a capture oligo, wherein a 3' terminus of each of the plurality of first strands includes a sequence of the capture oligo or a reverse complement thereto.

In another aspect, the present disclosure provides methods of assessing a sample of guide RNA molecules, comprising: (a) determining the nucleotide sequences of a plurality of guide RNA molecules of the sample; (b) comparing the nucleotide sequences of the plurality of guide RNA molecules to a reference guide RNA sequence to identify truncation variants and/or sequence variants, relative to the reference guide RNA sequence; (c) determining (e.g., calculating) a level (e.g., a fraction of total nucleotide sequences) of truncation variants comprising a truncation (e.g., a truncation at a 5' end), relative to the reference guide RNA sequence; (d) determining (e.g., calculating) a level (e.g., a fraction of total nucleotide sequences) of sequence variants comprising one or more of a nucleotide substitution, insertion or deletion, relative to the reference guide RNA sequence, within the 100, 30, or 20 nucleotides proximate to a 5' end of the reference guide RNA sequence and/or within a bulge region of the reference guide RNA sequence and/or within a *nexus* region of the reference guide sequence; and (e) for each sequence variant guide RNA molecule present at a level greater than or equal to 0.1% (e.g., greater than or equal to 0.25%, 0.5%, 0.75%, 1%, 1.5%, 2%, 2.5%, 5%, 10%, 20%, 30%, 40%, or 50%), (i) identifying the nucleotide sequence of the targeting domain of the sequence variant; and (ii) determining one or more potential off-target sites for the targeting domain of the sequence variant.

In some embodiments, the guide RNA molecules and the reference guide RNA sequence comprise a targeting domain within the first 30 nucleotides.

In some embodiments, the reference guide RNA sequence is a *S. pyogenes* guide RNA sequence, and the method comprises determining the level of sequence variants comprising one or more of a nucleotide substitution, insertion or deletion within a region comprising nucleotide positions 55 to 60, relative to the reference guide RNA sequence. In some embodiments, the reference guide RNA sequence is a *S. pyogenes* guide RNA sequence, and the method comprises determining the level of sequence variants comprising one or more of a nucleotide substitution, insertion or deletion at nucleotide position 61, relative to the reference guide RNA sequence. In some embodiments, the reference guide RNA sequence is a *S. pyogenes* guide RNA sequence, and the method comprises determining the level of sequence variants comprising one or more of a nucleotide substitution, insertion or deletion within a region comprising nucleotide positions 27 to 28, relative to the reference guide RNA sequence. In some embodiments, the reference guide RNA sequence is a *S. pyogenes* guide RNA sequence, and the method comprises determining the level of sequence variants comprising one or more of a nucleotide substitution, insertion or deletion within a region comprising nucleotide positions 40 to 43, relative to the reference guide RNA sequence. In some embodiments, the reference guide RNA sequence is a *S. pyogenes* guide RNA sequence, and the method comprises determining the level of sequence variants comprising one or more of a nucleotide substitution, insertion or deletion at nucleotide positions 27, 28, and 40 to 43, relative to the reference guide RNA sequence.

In some embodiments, the method further comprises assigning a value to the sample of guide RNA molecules based on the determined level of truncation variants and/or sequence variants. In some embodiments, the method further comprises assigning a mismatch frequency to the sample of guide RNA molecules based on the determined level of truncation variants and/or sequence variants.

In some embodiments, the sample comprises less than about 95%, 90%, 80%, 70%, 60%, 50%, 40%, 30%, 20%, or 10% of truncation variants, e.g., less than about 5%, 4%, 3%, 2%, 1%, 0.5%, or 0.1% of truncation variants.

In some embodiments, the sample comprises less than about 95%, sequence variants (e.g., less than about 90%, 80%, 70%, 60%, 50%, 40%, 30%, 20%, 10%, 5%, 1%, 0.5%, 0.3%, or 0.1% of sequence variants).

In some embodiments, determining one or more potential off-target sites for the targeting domain of a sequence variant comprises performing an in silico assessment. In some embodiments, none of the sequence variants present at a level greater than or equal to 50%, 40%, 30%, 20%, 10%, 5%, 2%, 1.5%, 1%, 0.75%, 0.25%, or 0.1% comprises a targeting domain for a potential off-target site.

In some embodiments, determining the nucleotide sequences of the plurality of guide RNA molecules comprises combining (i) the plurality of guide RNA molecules; (ii) one or more template switching oligonucleotides comprising a 3' hybridization domain and a sequence adapter; (iii) a retroviral reverse transcriptase; and (iv) dNTPs; in a reaction mixture under conditions sufficient to produce a plurality of product nucleic acids, each product nucleic acid comprising (i) a guide RNA molecule and (ii) the one or more template switching oligonucleotides, each hybridized to adjacent regions of a single product nucleic acid comprising a region polymerized from the dNTPs by the retroviral reverse transcriptase, wherein the region polymerized from the dNTPs comprises a domain that is complementary to and hybridized to the 5' end of the guide RNA molecule.

In some embodiments, the guide RNA molecules are non-polyadenylated, and the method further comprises polyadenylating the 3' ends of the non-polyadenylated guide RNA molecules. In some embodiments, the 3' hybridization domain comprises one or more locked nucleic acids (LNAs) at the 3' end.

In some embodiments, the 3' hybridization domain comprises a homo-trinucleotide, e.g., guanine nucleotides. In some embodiments, the 3' hybridization domain comprises a hetero-trinucleotide.

In some embodiments, the one or more template switching oligonucleotides comprise a predetermined 5' deoxyribonucleotide sequence and a 3' hybridization domain comprising a homo-tri-ribonucleotide or a hetero-tri-ribonucleotide.

In some embodiments, the method comprises combining: (i) the plurality of guide RNA molecules; and (ii) a heterogeneous mixture of template switching oligonucleotides comprising a 3' hybridization domain and a sequence adapter and wherein the 3' hybridization domains comprise a partially degenerate sequence of guanine nucleotides and cytosine nucleotides (SSS).

In some embodiments, the one or more template switching oligonucleotides comprise a 5' domain comprising one or more isomers of guanine nucleotides or cytosine nucleotides, and/or the one or more template switching oligonucleotides comprise one or more 5'-methylated deoxycytidines, and/or the one or more template switching oligonucleotides comprise a unique molecular identifier (e.g., comprising a degenerate sequence comprising from about 1 to about 20 nucleotides, from about 1 to about 10 nucleotides, from about 5 to about 15 nucleotides, from about 10 nucleotides).

In some embodiments, the one or more template switching oligonucleotides comprise a tag (e.g., comprising two, three, four, five, six nucleotides, e.g., comprising a fixed four base tag).

In some embodiments, the sequence adapter comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof. In some embodiments, the identifying steps and/or determining steps comprise identifying the unique molecular identifier.

In some embodiments, the method further comprises contacting a 3' region of the single product nucleic acid complementary to the one or more template switching oligonucleotides with a second strand primer configured to bind thereto under hybridization conditions. In some embodiments, the method further comprises subjecting the reaction mixture to nucleic acid polymerization conditions following contacting the 3' region of the single product nucleic acid complementary to the one or more template switching oligonucleotides with the second strand primer.

In some embodiments, the method further comprises contacting the guide RNA molecules with a first primer that primes the synthesis of the single product nucleic acid. In some embodiments, the first primer comprises a first domain that hybridizes to the guide RNA molecules and a second domain that does not hybridize to the guide RNA molecules. In some embodiments, the first domain has a defined sequence. In some embodiments, the first domain comprises thymine nucleotides and/or the second domain comprises a sequence adapter. In some embodiments, the sequence adapter of the second domain comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof. In some embodiments, the sequence adapter of the second domain is different from the sequence adapter of the one or more template switching oligonucleotides.

In some embodiments, the method further comprises subjecting the single product nucleic acid to nucleic acid amplification conditions. In some embodiments, the single product nucleic acid comprises an amplification sequence at its 5' end and an amplification sequence at its 3' end, and wherein subjecting the single product nucleic acid to nucleic acid amplification conditions comprises amplifying the single product nucleic acid with primers complementary to the 5' and 3' amplification sequences. In some embodiments, one or both of the primers complementary to the 5' and the 3' amplification sequences comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof.

In some embodiments, the method further comprises performing next generation sequencing on the plurality of single product nucleic acids.

In some embodiments, the reaction mixture comprises about 10-250 ng of guide RNA molecules.

In some embodiments, the guide RNA molecules comprise a 5' modification (e.g., a 5' ARCA cap or a 5' inverted G cap). Additionally or alternatively, in some embodiments, the guide RNA molecules comprise a 3' polyA tail. Additionally or alternatively, in some embodiments, the guide RNA molecules comprise a urea linkage, a bromoacetyl-thiol linkage, or a phosphorothioate linkage. In some embodiments, the guide RNA molecules comprise a 2'-O-methyl (2' OMe).

In another aspect, the present disclosure provides methods of manufacturing a therapeutic preparation of guide RNA molecules, comprising: determining the nucleotide sequences of a plurality of guide RNA molecules of a sample; comparing the nucleotide sequences of the guide RNA molecules to a reference guide RNA sequence; and formulating at least a portion of the sample of guide RNA molecules into a therapeutic preparation if: (a) the sample comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants comprising a truncation at a 5' end, relative to the reference guide RNA sequence; (b) the sample comprises less than about 95% sequence variants (e.g., less than about 90%, 80%, 70%, 60%, 50%, 40%, 30%, 20%, 10%, 5%, 1%, 0.5%, 0.3%, or 0.1% of sequence variants) comprising a nucleotide substitution, insertion or deletion, relative to the reference guide RNA sequence, within the first 100, 30, or 20 nucleotides of the guide RNA molecule; and/or (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site. In some embodiments, the guide RNA molecules and the reference guide RNA sequence comprise a targeting domain within the first 30 nucleotides.

In some embodiments, the method comprises formulating at least a portion of the sample of guide RNA molecules into a therapeutic preparation if the sample comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants.

In some embodiments, the method comprises formulating at least a portion of the sample of guide RNA molecules into a therapeutic preparation if the sample comprises less than about 95% sequence variants (e.g., less than about 90%, 80%, 70%, 60%, 50%, 40%, 30%, 20%, 10%, 5%, 1%, 0.5%, 0.3%, or 0.1% sequence variants).

In some embodiments, the method further comprises determining the level of truncation variants. In some embodiments, the method further comprises determining the level of sequence variants.

In some embodiments, the method further comprises, for each sequence variant present at a level greater than or equal to 50%, 40%, 30%, 20%, 10%, 5%, 2%, 1.5%, 1%, 0.75%, 0.25%, or 0.1%, (i) identifying the nucleotide sequence of the targeting domain of the sequence variant; and (ii) determining one or more potential off-target sites for the targeting domain of the sequence variant. In some embodiments, determining one or more potential off-target sites for the targeting domain of a variant guide RNA molecule comprises performing an in silico assessment.

In some embodiments, determining the nucleotide sequences of the plurality of guide RNA molecules comprises combining: the plurality of guide RNA molecules; a template switching oligonucleotide comprising a 3' hybridization domain and a sequence adapter; a retroviral reverse transcriptase; and dNTPs; in a reaction mixture under conditions sufficient to produce a plurality of product nucleic acids, each product nucleic acid comprising (i) a guide RNA molecule and (ii) the template switching oligonucleotide, each hybridized to adjacent regions of a single product nucleic acid comprising a region polymerized from the dNTPs by the retroviral reverse transcriptase, wherein the region polymerized from the dNTPs comprises a domain that is complementary to and hybridized to the 5' end of the guide RNA molecule.

In some embodiments, the guide RNA molecules are non-polyadenylated, and the method further comprises polyadenylating the 3' ends of the non-polyadenylated guide RNA molecules.

In some embodiments, the 3' hybridization domain comprises a homo-trinucleotide, e.g., guanine nucleotides. In some embodiments, the 3' hybridization domain comprises a hetero-trinucleotide.

In some embodiments, the sequence adapter comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof.

In some embodiments, the method further comprises contacting a 3' region of the single product nucleic acid complementary to the template switching oligonucleotide with a second strand primer configured to bind thereto under hybridization conditions. In some embodiments, the method further comprises subjecting the reaction mixture to nucleic acid polymerization conditions following contacting the 3' region of the single product nucleic acid complementary to the template switching oligonucleotide with the second strand primer.

In some embodiments, the method further comprises contacting the guide RNA molecules with a first primer that primes the synthesis of the single product nucleic acid. In some embodiments, the first primer comprises a first domain that hybridizes to the guide RNA molecules and a second domain that does not hybridize to the guide RNA molecules. In some embodiments, the first domain has a defined sequence. In some embodiments, the first domain comprises thymine nucleotides. In some embodiments, the second domain comprises a sequence adapter.

In some embodiments, the sequence adapter of the second domain comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof. In some embodiments, the sequence adapter of the second domain is different from the sequence adapter of the template switching oligonucleotide.

In some embodiments, the method further comprises subjecting the single product nucleic acid to nucleic acid amplification conditions. In some embodiments, the single product nucleic acid comprises an amplification sequence at its 5' end and an amplification sequence at its 3' end, and wherein subjecting the single product nucleic acid to nucleic acid amplification conditions comprises amplifying the single product nucleic acid with primers complementary to the 5' and 3' amplification sequences.

In some embodiments, one or both of the primers complementary to the 5' and the 3' amplification sequences comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof.

In some embodiments, the method further comprises performing next generation sequencing on the plurality of single product nucleic acids.

In some embodiments, the reaction mixture comprises about 10-250 ng of guide RNA molecules.

In some embodiments, the guide RNA molecules comprise a 5' modification, e.g., a 5' ARCA cap.

In some embodiments, the guide RNA molecules comprise a 3' polyA tail.

In some embodiments, the guide RNA molecules comprise a urea linkage or a bromoacetyl-thiol linkage.

In another aspect, the disclosure features a method of assessing a composition comprising guide RNA molecules, comprising (i) determining the nucleotide sequences of a plurality of guide RNA molecules of a sample of the composition; (ii) comparing the nucleotide sequences of the guide RNA molecules to a reference guide RNA sequence; and (iii) producing a ribonucleoprotein (RNP) complex comprising a Cas9 molecule and a guide RNA molecule from the composition, if: (a) the sample comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants comprising a truncation at a 5' end, relative to the reference guide RNA sequence; (b) the sample comprises less than about 95% sequence variants (e.g., less than about 90%, 80%, 70%, 60%, 50%, 40%, 30%, 20%, 10%, 5%, 1%, 0.5%, 0.3%, or 0.1% of sequence variants) comprising a nucleotide substitution, insertion or deletion, relative to the reference guide RNA sequence, within the first 100, 30, or 20 nucleotides of the guide RNA molecule; and/or (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site.

In another aspect, the disclosure features a method of administering a composition comprising guide RNA molecules, comprising (i) determining the nucleotide sequences of a plurality of guide RNA molecules of a sample of the composition; (ii) comparing the nucleotide sequences of the guide RNA molecules to a reference guide RNA sequence; and (iii) administering to a subject in need thereof a ribonucleoprotein (RNP) complex comprising a Cas9 molecule and a guide RNA molecule from the composition, if: (a) the sample comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants comprising a truncation at a 5' end, relative to the reference guide RNA sequence; (b) the sample comprises less than about 95% sequence variants (e.g., less than about 90%, 80%, 70%, 60%, 50%, 40%, 30%, 20%, 10%, 5%, 1%, 0.5%, 0.3%, or 0.1% of sequence variants) comprising a nucleotide substitution, insertion or deletion, relative to the reference guide RNA sequence, within the first 100, 30, or 20 nucleotides of the guide RNA molecule; and/or (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site.

In another aspect, the disclosure features a method of administering a composition comprising guide RNA molecules, comprising (i) determining the nucleotide sequences of a plurality of guide RNA molecules of a sample of the composition; (ii) comparing the nucleotide sequences of the guide RNA molecules to a reference guide RNA sequence; and (iii) administering to a subject in need thereof a guide RNA molecule from the composition and a Cas9 molecule, if: (a) the sample comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants comprising a truncation at a 5' end, relative to the reference guide RNA sequence; (b) the sample comprises less than about 95% sequence variants (e.g., less than about 90%, 80%, 70%, 60%, 50%, 40%, 30%, 20%, 10%, 5%, 1%, 0.5%, 0.3%, or 0.1% of sequence variants) comprising a nucleotide substitution, insertion or deletion, relative to the reference guide RNA sequence, within the first 100, 30, or 20 nucleotides of the guide RNA molecule; and/or (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site.

In another aspect, the invention features a composition comprising guide RNA molecules, wherein (a) the composition comprises less than about 95%, 90%, 80%, 70%, 60%, 50%, 40%, 30%, 20%, or 10%, e.g., less than about 5%, 4%, 3%, 2%, 1%, 0.5%, or 0.1% of truncation variants comprising a truncation at a 5' end, relative to the reference guide RNA sequence; and/or (b) the composition comprises less than about 95% sequence variants (e.g., less than about 90%, 80%, 70%, 60%, 50%, 40%, 30%, 20%, 10%, 5%, 1%, 0.5%, 0.3%, or 0.1% of sequence variants) comprising a nucleotide substitution, insertion or deletion, relative to the reference guide RNA sequence, within the first 100, 30, or 20 nucleotides of the guide RNA molecule; and/or (c) if the composition comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site.

BRIEF DESCRIPTION OF THE DRAWING

FIGS. 2A-2C are electrophoretic traces depicting data of generation of robust dsDNA products from low input material. A BioAnalyzer (BioA) instrument was used to perform automated gel electrophoresis and laser-induced fluorescence as quality control (QC) for dsDNA PCR products generated from reverse transcription of gRNA. Sequencing adapter sequences added 153 bp to RNA-derived sequences (Expected size=~250 bp (97-100mer+153 bp)). Main peaks shown in FIGS. 2A-2C are indicative of a desired product.

DEFINITIONS

Figure 1:
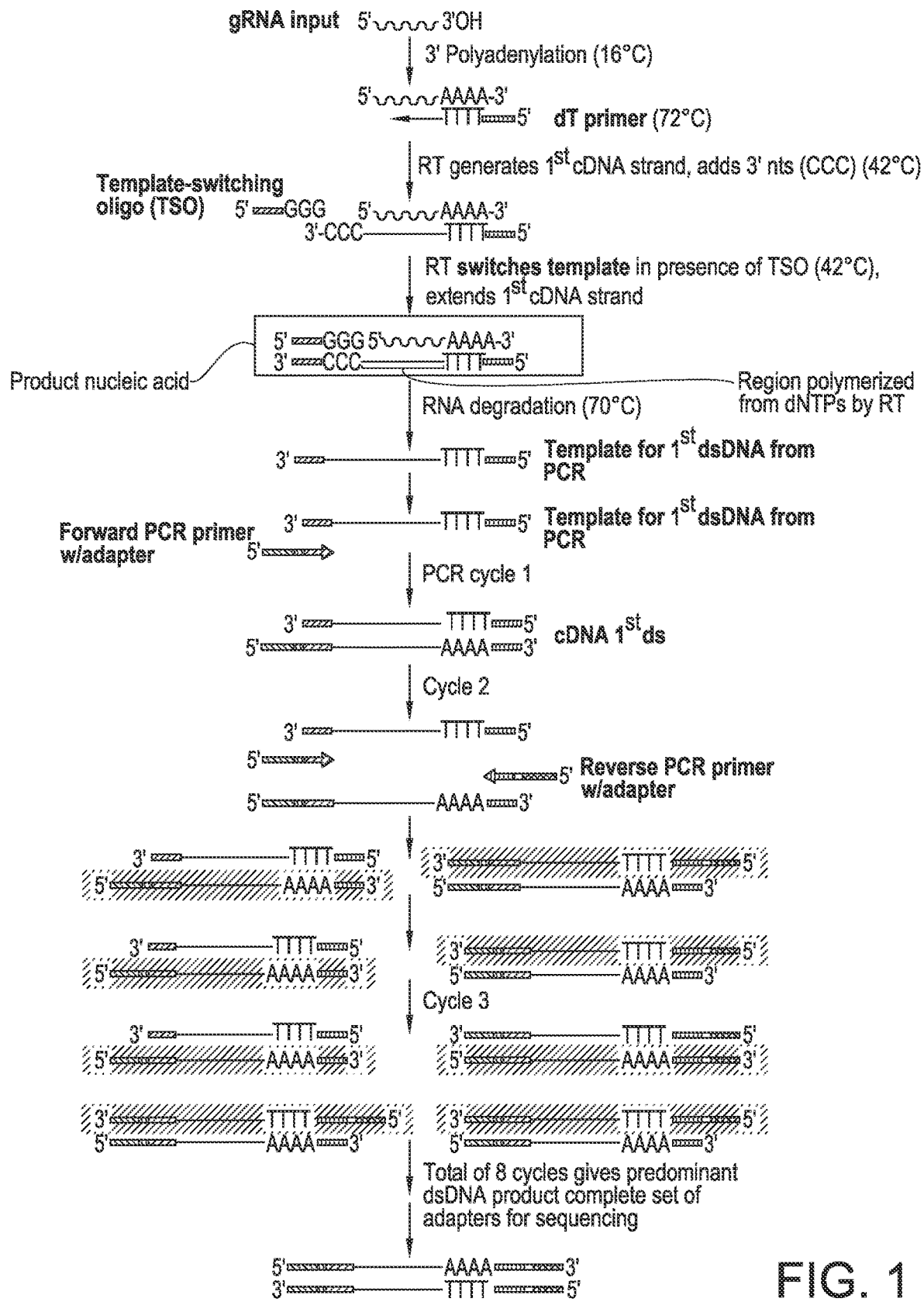
FIG. 1 depicts a schematic of a template-switching scheme, according to an illustrative embodiment of the invention.

Throughout the specification, several terms are employed that are defined in the following paragraphs. Other definitions may also found within the body of the specification. In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the terms "about" and "approximately," in reference to a number, is used herein to include numbers that fall within a range of 20%, 10%, 5%, or 1% in either direction (greater than or less than) of the number unless otherwise stated or otherwise evident from the context (except where such number would exceed 100% of a possible value).

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, the term "nuclease" refers to a polypeptide capable of cleaving the phosphodiester bonds between the nucleotide subunits of nucleic acids; the term "endonuclease" refers to a polypeptide capable of cleaving the phosphodiester bond within a polynucleotide chain.

As used herein, the terms "nucleic acid", "nucleic acid molecule" or "polynucleotide" are used herein interchangeably. They refer to a polymer of deoxyribonucleotides or ribonucleotides in either single- or double-stranded form, and unless otherwise stated, encompass known analogs of natural nucleotides that can function in a similar manner as naturally occurring nucleotides. The terms encompass nucleic acid-like structures with synthetic backbones, as well as amplification products. DNAs and RNAs are both polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

As used herein, the term "oligonucleotide" refers to a string of nucleotides or analogues thereof. Oligonucleotides may be obtained by a number of methods including, for example, chemical synthesis, restriction enzyme digestion or PCR. As will be appreciated by one skilled in the art, the length of an oligonucleotide (i.e., the number of nucleotides) can vary widely, often depending on the intended function or use of the oligonucleotide. Generally, oligonucleotides comprise between about 5 and about 300 nucleotides, for example, between about 15 and about 200 nucleotides, between about 15 and about 100 nucleotides, or between about 15 and about 50 nucleotides. Throughout the specification, whenever an oligonucleotide is represented by a sequence of letters (chosen from the four base letters: A, C, G, and T, which denote adenosine, cytidine, guanosine, and thymidine, respectively), the nucleotides are presented in the 5' to 3' order from the left to the right. In certain embodiments, the sequence of an oligonucleotide includes one or more degenerate residues described herein.

As used herein, the term "polypeptide" generally has its art-recognized meaning of a polymer of amino acids. The term is also used to refer to specific functional classes of polypeptides, such as, for example, nucleases, antibodies, etc.

As used herein, the term "target site," refers to a nucleic acid sequence that defines a portion of a nucleic acid to which a binding molecule will bind, provided sufficient conditions for binding exist. In some embodiments, a target site is a nucleic acid sequence to which a nuclease described herein binds and/or that is cleaved by such nuclease. In some embodiments, a target site is a nucleic acid sequence to which a guide RNA described herein binds. A target site may be single-stranded or double-stranded. In the context of nucleases that dimerize, for example, nucleases comprising a FokI DNA cleavage domain, a target site typically comprises a left-half site (bound by one monomer of the nuclease), a right-half site (bound by the second monomer of the nuclease), and a spacer sequence between the half sites in which the cut is made. In some embodiments, the left-half site and/or the right-half site is between 10-18 nucleotides long. In some embodiments, either or both half-sites are shorter or longer. In some embodiments, the left and right half sites comprise different nucleic acid sequences. In the context of zinc finger nucleases, target sites may, in some embodiments, comprise two half-sites that are each 6-18 bp long flanking a non-specified spacer region that is 4-8 bp long. In the context of TALENs, target sites may, in some embodiments, comprise two half-sites sites that are each 10-23 bp long flanking a non-specified spacer region that is 10-30 bp long. In the context of RNA-guided (e.g., RNA-programmable) nucleases, a target site typically comprises a nucleotide sequence that is complementary to a guide RNA of the RNA-programmable nuclease, and a protospacer adjacent motif (PAM) at the 3' end or 5' end adjacent to the guide RNA-complementary sequence. For the RNA-guided nuclease Cas9, the target site may be, in some embodiments, 16-24 base pairs plus a 3-6 base pair PAM (e.g., NNN, wherein N represents any nucleotide). Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., S. thermophilus instead of S. pyogenes) recognizes a PAM that comprises the sequence NGGNG. Additional PAM sequences are known, including, but not limited to NNAGAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [Nz]-[PAM], where each N is, independently, any nucleotide, and z is an integer between 1 and 50. In some embodiments, z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20.

The term "variant" refers to an entity such as a polypeptide or polynucleotide that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. In some embodiments, a "variant" is a DNA or RNA sequence that differs from a reference sequence in one or more nucleotides, e.g., by one or more substitutions, insertions, deletions or any other changes. In some embodiments, a "truncation variant" refers to a variant that is truncated at a 5' end, relative to a reference sequence. In some embodiments, a "sequence variant" refers to a variant that includes one or more substitutions, insertions, or deletions within an internal region, relative to a reference sequence.

DETAILED DESCRIPTION OF CERTAIN EMBODIMENTS

Overview

Most gRNAs are currently synthesized by one of two methods: in-vitro transcription (IVT) and chemical synthesis. IVT typically involves the transcription of RNA from a DNA template by means of a bacterial RNA polymerase such as T7 polymerase. However, IVT synthesis may not be suitable for all guide RNA sequences: the T7 polymerase tends to transcribe sequences which initiate with a 5' guanine more efficiently than those initiated with another 5' base, and may recognize stem-loop structures followed by poly-uracil tracts, which structures are present in certain gRNAs, as a signal to terminate transcription, resulting in truncated guide RNA transcripts. Chemical synthesis, on the other hand, is inexpensive and GMP-production for shorter oligonucleotides (e.g., less than 100 nucleotides in length) is readily available. Chemical synthesis methods are described throughout the literature, for instance by Beaucage and Carruthers, Curr Protoc Nucleic Acid Chem. 2001 May; Chapter 3: Unit 3.3 (Beaucage & Carruthers). These methods typically involve the stepwise addition of reactive nucleotide monomers until an oligonucleotide sequence of a desired length is reached.

Whatever method is utilized, synthetic gRNAs may include contaminant species that vary, in length and/or sequence, from the desired synthesis product. Contaminants can include truncation species (such as 5' truncations), nucleotide substitutions, insertions, and/or deletions. These changes can occur throughout the gRNA molecule, but may particularly affect the sequence in or near the 5' targeting domain of Cas9 gRNAs, the bulge region, and/or the *nexus* region. The presence of contaminant species may reduce the activity and/or alter the specificity of synthetic gRNA compositions, potentially complicating their use in applications which depend critically on gRNA activity and/or specificity, such as therapeutics.

Methods and systems of the disclosure can be used to assess the presence of contaminating species within gRNA compositions and, consequently, to predict the activity and specificity of these compositions. For example, methods and systems described herein can be used to determine, for a guide RNA composition, a frequency of sequence length variation within the composition, and to characterize variants such as truncations, internal insertions or deletions, etc., relative to a reference guide RNA sequence corresponding, for example, to a desired gRNA synthesis product. Methods and systems described herein can also be used to determine the frequency of sequence identity variation within a gRNA composition and to characterize the incidence of specific base variations and/or length variations at individual positions within the gRNA molecules in the composition. This characterization is, again, relative to a reference guide RNA molecule.

Generally, methods of the disclosure include preparing a cDNA library from a sample of gRNAs, followed by sequencing of the library. A cDNA library can be prepared using a method that transcribes full-length gRNA, including the entire targeting domain sequence (e.g., through the 5' terminus of the gRNA), e.g., by strand extension, or by ligation of an adapter or other sequence, resulting in a cDNA library that is representative of the diversity of gRNA species in the sample. For example, a cDNA library can be produced from a gRNA sample using a template switching oligonucleotide and template switching nucleic acid polymerase, as described herein. The diversity of produced cDNA libraries can be assessed using known methods, e.g., by a barcode domain or a molecular identification domain as described herein into the cDNAs. Sequence adapters can also be incorporated into the cDNAs (e.g., using primers described herein) and used to sequence individual cDNAs of the library (e.g., using a sequencing platform of interest).

After sequences of individual cDNAs are determined, methods can include comparing determined cDNA sequences to a reference sequence, e.g., a sequence of the expected synthesized gRNA, to determine presence and/or identity of contaminant species (i.e., a cDNA generated from a gRNA that differs from the reference sequence). For example, determined cDNA sequences can be aligned with the expected reference sequence to analyze or identify differences between determined cDNA sequences and the reference sequence. Some methods include alignment of cDNA sequences to the expected synthesis product, and characterization of the contaminant species, including, e.g., (i) assessing the frequency, among the determined cDNA sequences, of non-expected bases at one or more certain positions and/or in one or more certain regions of the gRNA, e.g., the targeting domain, and/or (ii) assessing the frequency, among the determined cDNA sequences, of sequence length variances at one or more certain positions and/or in one or more certain regions. Frequency assessment can be performed using known relevant statistical or analytical approaches. For example, the frequencies of particular categories of contaminant species can be aggregated into a relevant measure, such as % of determined sequences with non-expected bases (relative to the reference sequence) within the targeting domain, *nexus* region, and/or bulge region, and/or % of determined sequences that include a 5' truncation (relative to the reference sequence).

Moreover, data (e.g., a measure described herein) generated by provided methods and systems for a gRNA sample can be compared to a predetermined threshold value to determine a relevant characteristic of the gRNA sample, e.g., to confirm the identity and/or quality of a composition or preparation of gRNAs. For example, frequency of determined sequences that include a 5' truncation can be compared to a predetermined threshold value to determine, produce, or provide activity/efficacy information for the gRNA sample, such as for therapeutic applications. In some embodiments, a gRNA sample that includes 5' truncations at frequency under 95% (e.g., under 90%, 80%, 70%, 60%, 50%, 40%, 30%, 20%, 10%, 9%, 8%, 7%, 6%, or 5%) meets an acceptable level of activity/efficacy. Additionally or alternatively, frequency of determined sequences that include a non-expected base within the targeting domain, the bulge region, and/or the *nexus* region can be compared to a predetermined threshold value to determine, produce, or provide specificity/safety information for the gRNA sample, such as for therapeutic applications. In some embodiments, a gRNA sample meets an acceptable level of specificity/safety where (i) at least 5% (e.g., 10%, 20%, 30%, 40%, 50%, 60%, 70%, 80%, 90%, 95%, 96%, 97%, 98%, or 99%) of full-length sequences (e.g., that are determined to be full-length) have 100% sequence identity to the reference sequence across the length of the targeting domain, the bulge region and/or the *nexus* region, and/or (ii) the major contaminant gRNA species are determined or predicted to exhibit no off-target activity.

Assessment Methods

The present disclosure provides, among other things, methods and systems for assessing a composition of guide RNA molecules for presence of contaminants, e.g., guide RNAs that include one or more truncations (e.g., at a 5' end), substitutions, insertions, and/or deletions (e.g., within a targeting domain, a bulge region and/or a *nexus* region), relative to a reference sequence.

In one aspect, the disclosure provides selection and/or quality control criteria, which can be used to identify and/or qualify a guide RNA composition, e.g., for potential therapeutic purposes. For example, a composition can be selected or identified as sufficiently pure, selected or identified for processing, and/or can be processed into a therapeutic product, if (a) the sample comprises less than about 95%, 90%, 80%, 70%, 60%, 50%, 40%, 30%, 20%, 10%, 5%, 4%, 3%, 2%, 1%, 0.5%, or 0.1% of truncation variants comprising a truncation at a 5' end, relative to a reference guide RNA sequence; and/or (b) the sample comprises less than about 95% (e.g., less than about 90%, 80%, 70%, 60%, 50%, 40%, 30%, 20%, 10%, 5%, 1%, 0.5%, 0.3%, or 0.1% of sequence variants comprising a nucleotide substitution, insertion and/or deletion, relative to a reference guide RNA sequence, within the first 100, 30, or 20 nucleotides, within the bulge region, and/or within the *nexus* region of the guide RNA molecule; and/or (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site. In some embodiments, a composition can be selected or identified as sufficiently pure, selected or identified for processing, and/or processed into a therapeutic product, if (a) the sample comprises less than about 95%, 90%, 80%, 70%, 60%, 50%, 40%, 30%, 20%, 10%, 5%, 4%, 3%, 2%, 1%, 0.5%, or 0.1% truncation variants, relative to the reference guide RNA sequence; (b) the sample comprises less than about 95% (e.g., less than about 90%, 80%, 70%, 60%, 50%, 40%, 30%, 20%, 10%, 5%, 1%, 0.5%, 0.3%, or 0.1% of sequence variants comprising a nucleotide substitution, insertion and/or deletion, relative to the reference guide RNA sequence, within the first 100, 30, or 20 nucleotides, within the bulge region and/or within the *nexus* region of the guide RNA molecule; and (c) if the sample comprises a sequence variant present at a level greater than or equal to 50%, 40%, 30%, 20%, 10%, 5%, 2%, 1.5%, 1%, 0.75%, 0.25%, or 0.1%, the sequence variant does not comprise a targeting domain for a potential off-target site.

In another aspect, the disclosure provides selection and/or quality control criteria, which can be used to identify a guide RNA composition as unsuitable, and/or disqualify a guide RNA composition, e.g., for potential therapeutic purposes. For example, a composition can be selected or identified as not sufficiently pure, deselected for processing, and/or not processed into a therapeutic product, if (a) the sample comprises more than about 0.1%, 0.5%, 1%, 2%, 3%, 4%, 5%, 10%, 20%, 30%, 40%, 50%, 60%, 70%, 80%, 90%, or 95% of truncation variants comprising a truncation at a 5' end, relative to the reference guide RNA sequence; and/or (b) the sample comprises more than about 0.1%, 0.3%, 0.5%, 1%, 5%, 10%, 20%, 30%, 40%, 50%, 60%, 70%, 80%, 90%, or 95% of sequence variants comprising a nucleotide substitution, insertion and/or deletion, relative to the reference guide RNA sequence, within the first 100, 30, or 20 nucleotides, within the bulge region and/or within the *nexus* region of the guide RNA molecule; and/or (c) if the sample comprises a sequence variant present at a level greater than or equal to 0.1%, 0.25%, 0.5%, 0.75%, 1%, 1.5%, 2%, 5%, 10%, 20%, 30%, 40%, or 50%, the sequence variant comprises a targeting domain for a potential off-target site. In some embodiments, a composition can be selected or identified as not sufficiently pure, deselected for processing, and/or not processed into a therapeutic product, if (a) the sample comprises more than about 0.1%, 0.5%, 1%, 2%, 3%, 4%, 5%, 10%, 20%, 30%, 40%, 50%, 60%, 70%, 80%, 90% or 95% of truncation variants comprising a truncation at a 5' end, relative to the reference guide RNA sequence; (b) the sample comprises more than about 0.1%, 0.3%, 0.5%, 1%, 5%, 10%, 20%, 30%, 40%, 50%, 60%, 70%, 80%, 90%, or 95% of sequence variants comprising a nucleotide substitution, insertion and/or deletion, relative to the reference guide RNA sequence, within the first 100, 30, or 20 nucleotides, within the bulge region and/or within the *nexus* region of the guide RNA molecule; and (c) if the sample comprises a sequence variant present at a level greater than or equal to 0.1%, 0.25%, 0.5%, 0.75%, 1%, 1.5%, 2%, 5%, 10%, 20%, 30%, 40%, or 50%, the sequence variant comprises a targeting domain for a potential off-target site.

In some instances, methods disclosed herein can be used to confirm the identity and/or quality of a composition or preparation of gRNAs. For example, methods can include assessing one or more preparations (e.g., one or more samples, lots, and/or batches) of a gRNA, e.g., to confirm whether a preparation of gRNAs qualifies as sufficiently pure, and, optionally, qualifying the preparation if qualifying criteria (e.g., predefined qualifying criteria described herein) are met; thereby evaluating, identifying, and/or producing (e.g., manufacturing) a composition or preparation of gRNAs.

Methods of the disclosure have a variety of applications and include, e.g., quality control, analysis of a preparation of gRNAs prior to and/or after completion of manufacture (e.g., prior to or after distribution to a fill/finish environment or facility), prior to or after release into commerce (e.g., before distribution to a pharmacy, a caregiver, a patient, or other end-user). Evaluations from methods described herein are useful for guiding, controlling or implementing a number of activities or steps in the process of making, distributing, and monitoring and providing for the safe and efficacious use of a preparation of gRNAs. Thus, in an embodiment, e.g., responsive to the evaluation, e.g., depending on whether a criterion is met, a decision or step is taken. The method can further comprise one or both of the decision to take the step and/or carrying out the step itself. E.g., the step can comprise one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation (e.g., another batch) of the gRNA; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject. For example, based on the result of a determination described herein, or upon comparison to a reference standard, the batch from which the preparation is taken can be processed, e.g., as described herein.

In some embodiments, one or more assessment, determination, and/or level described herein can be recorded in a print or computer-readable medium, e.g., in a test report, Material Safety Data Sheet (MSDS), batch record, Certificate of Testing (CofT) or Certificate of Analysis (CofA), for a composition of gRNAs.

Genome Editing Systems

The term "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

Naturally occurring CRISPR systems are organized evolutionarily into two classes and five types (Makarova et al. Nat Rev Microbiol. 2011 June; 9(6): 467-477 ("Makarova")), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multi-domain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e., target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g. administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. ("Maeder") describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino") describes a genome editing system that utilizes two gRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant") describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932, Mar. 11, 2014 ("Davis") (describing Alt-HDR); Frit et al. DNA Repair 17(2014) 81-97 ("Frit") (describing Alt-NHEJ); and Iyama and Wilson III, DNA Repair (Amst.) 2013-Aug.; 12(8): 620-636 ("Iyama") (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g., fused to) a cytidine deaminase functional domain, and may operate by generating targeted C-to-A substitutions. Exemplary nuclease/deaminase fusions are described in Komor et al. Nature 533, 420-424 (19 May 2016) ("Komor"). Alternatively, a genome editing system may utilize a cleavage-inactivated (i.e., a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 ("Briner")), and in Cotta-Ramusino.

In bacteria and archaea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g., GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science Aug. 17; 337(6096): 816-821 ("Jinek 2012")).

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu")), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 ("Nishimasu 2014") and Nishimasu et al., Cell 162, 1113-1126, Aug. 27, 2015 ("Nishimasu 2015")). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "*nexus*" (Briner). One or more additional stem loop structures are generally present near the 3' end of the gRNA, with the number varying by species: *S. pyogenes* gRNAs typically include two 3' stem loops (for a total of four stem loop structures including the repeat:anti-repeat duplex), while *S. aureus* and other species have only one (for a total of three stem loop structures).

Figure 10:
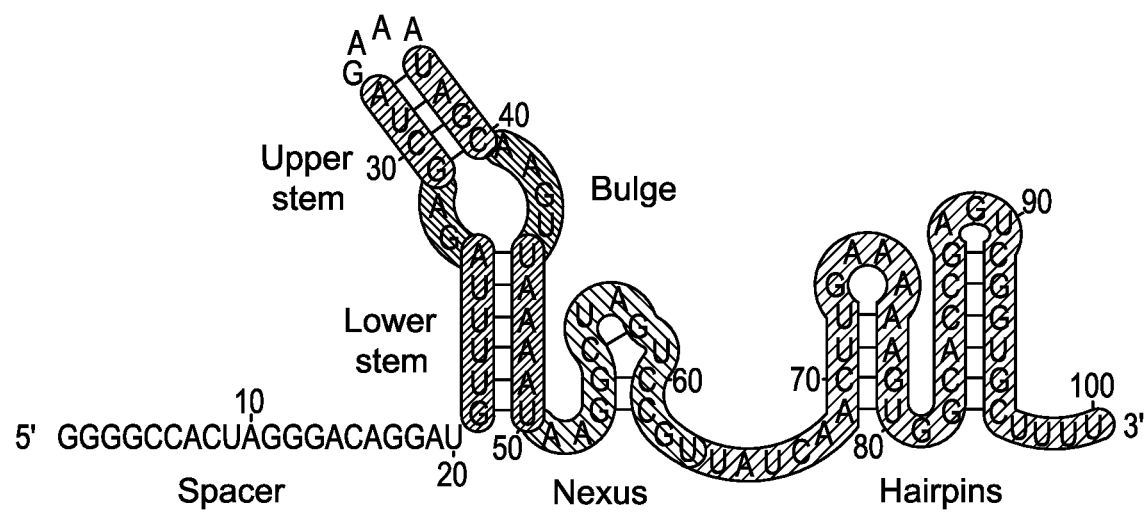
FIG. 10 is a schematic illustration of the six modules for the sgRNA of SpyCas9, from Briner et al. (Briner, Barrangou et al., Guide RNA Functional Modules Direct Cas9 Activity and Orthogonality, Molecular Cell 2014). The spacer region (black) typically comprises the first 20 bases on the 5' end and is responsible for targeting the DNA sequence of interest. The bulge (orange) is defined as the set of non-paired bases that are flanked by the upper (blue) and lower (green) stems which are formed by base pairs. Together the bulge, upper stem, and lower stem form the crRNA:tracrRNA duplex. The *nexus* region (pink) is defined as the stem loop downstream of the lower stem, when reading the gRNA sequence from 5' to 3'. The 3' end includes additional stem loops known as hairpins (purple).

FIG. 10 shows an overview and nomenclature of the six modules for the sgRNA of SpyCas9, from Briner. The spacer region (black) typically comprises the first 20 bases on the 5' end and is responsible for targeting the DNA sequence of interest. The bulge (orange) is defined as the set of non-paired bases that are flanked by the upper (blue) and lower (green) stems which are formed by base pairs. Together the bulge, upper stem, and lower stem form the crRNA:tracrRNA duplex. The *nexus* region (pink) is defined as the stem loop downstream of the lower stem, when reading the gRNA sequence from 5' to 3'. At the 3' end are additional stem loops known as hairpins (purple). FIG. 10 is an exemplary representation of the sgRNA of SpyCas9. Specific positions defining various regions of gRNAs for other Cas9 species are known in the art. For example, specific positions defining various regions of a guide RNA of *S. aureus* Cas9 include a "*nexus*"-like region from positions 57 to 67 and a "bulge" region from positions 30 and 43 to 45 (Nishimasu 2015). Although a "*nexus*" region is not referred to in *S. aureus* gRNAs, in some embodiments, principles used to describe a *nexus* region in guide RNAs of SpyCas9 extend to regions of guide RNAs of *S. aureus* Cas9.

In some embodiments, a gRNA is an engineered gRNA having one or more nucleotides inserted and/or deleted (e.g., upstream of the bulge region (e.g., before or within the spacer region), within the bulge region, between the bulge and *nexus* regions, and/or within the *nexus* region) relative to a reference gRNA. Additionally or alternatively, although the exemplary gRNA depicted in FIG. 10 includes 20 nucleotides in the spacer region, a gRNA (e.g., a gRNA for a Cas9 from a different species) can include a spacer region that has fewer than or more than 20 nucleotides. In instances in which a gRNA is engineered to include an insertion and/or deletion, or where a gRNA has a different number of nucleotides in any region, relative to a reference gRNA, it is within the skill of those in the art to determine the specific nucleotide positions that define any such region.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from *Prevotella* and Franciscella 1") is a recently discovered RNA-guided nuclease that does not require a tracrRNA to function. (Zetsche et al., 2015, Cell 163, 759-771 Oct. 22, 2015 ("Zetsche I")). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate, however, that although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA Design

Methods for selection and validation of target sequences as well as off-target analyses have been described previously, e.g., in *Mali*; Hsu; Fu et al., 2014 Nat biotechnol 32(3): 279-84, Heigwer et al., 2014 Nat methods 11(2):122-3; Bae et al. (2014) Bioinformatics 30(10): 1473-5; and Xiao A et al. (2014) Bioinformatics 30(8): 1180-1182. As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

For example, methods for selection and validation of target sequences as well as off-target analyses can be performed using cas-offinder (Bae S, Park J, Kim J-S. Cas-OFFinder: a fast and versatile algorithm that searches for potential off-target sites of Cas9 RNA-guided endonucleases. Bioinformatics. 2014; 30:1473-5). Cas-offinder is a tool that can quickly identify all sequences in a genome that have up to a specified number of mismatches to a guide sequence.

As another example, methods for scoring how likely a given sequence is to be an off-target (e.g., once candidate target sequences are identified) can be performed. An exemplary score includes a Cutting Frequency Determination (CFD) score, as described by Doench J G, Fusi N, Sullender M, Hegde M, Vaimberg E W, Donovan K F, et al. Optimized sgRNA design to maximize activity and minimize off-target effects of CRISPR-Cas9. Nat Biotechnol. 2016; 34:184-91.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides that can introduce stability toward nucleases. While not wishing to be bound by theory, it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

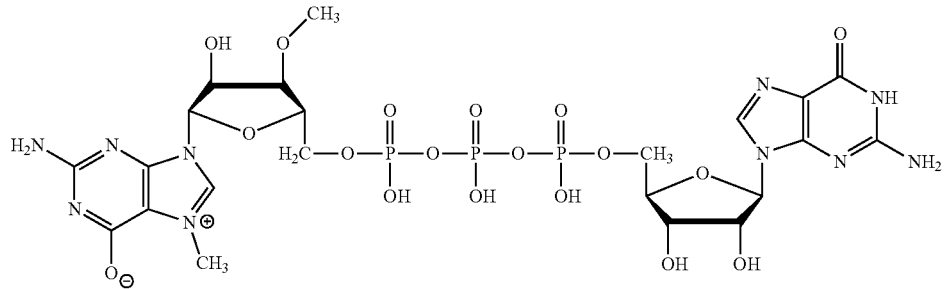

The cap or cap analog can be included during either chemical or enzymatic synthesis of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical or enzymatic synthesis, using a polyadenosine polymerase (e.g., *E. coli* Poly(A)Polymerase).

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

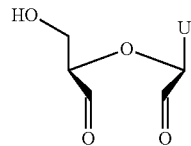

wherein "U" can be an unmodified or modified uridine.

The 3' terminal U ribose can be modified with a 2'3' cyclic phosphate as shown below:

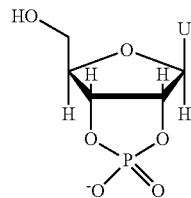

wherein "U" can be an unmodified or modified uridine.

Guide RNAs can contain 3' nucleotides that can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into a gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., $NH_2$, alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, including without limitation methylene, propylene, ether, or amino bridges; O-amino (wherein amino can be, e.g., $NH_2$, alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$, alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into a gRNA. In certain embodiments, 0- and N-alkylated nucleotides, e.g., N6-methyl adenosine, can be incorporated into a gRNA. In certain embodiments, one or more or all of the nucleotides in a gRNA are deoxynucleotides.

Guide RNAs can also include one or more cross-links between complementary regions of the crRNA (at its 3' end) and the tracrRNA (at its 5' end) (e.g., within a "tetraloop" structure and/or positioned in any stem loop structure occurring within a gRNA). A variety of linkers are suitable for use. For example, guide RNAs can include common linking moieties including, without limitation, polyvinylether, polyethylene, polypropylene, polyethylene glycol (PEG), polyvinyl alcohol (PVA), polyglycolide (PGA), polylactide (PLA), polycaprolactone (PCL), and copolymers thereof.

In some embodiments, a bifunctional cross-linker is used to link a 5' end of a first gRNA fragment and a 3' end of a second gRNA fragment, and the 3' or 5' ends of the gRNA fragments to be linked are modified with functional groups that react with the reactive groups of the cross-linker. In general, these modifications comprise one or more of amine, sulfhydryl, carboxyl, hydroxyl, alkene (e.g., a terminal alkene), azide and/or another suitable functional group. Multifunctional (e.g. bifunctional) cross-linkers are also generally known in the art, and may be either heterofunctional or homofunctional, and may include any suitable functional group, including without limitation isothiocyanate, isocyanate, acyl azide, an NHS ester, sulfonyl chloride, tosyl ester, tresyl ester, aldehyde, amine, epoxide, carbonate (e.g., Bis (p-nitrophenyl) carbonate), aryl halide, alkyl halide, imido ester, carboxylate, alkyl phosphate, anhydride, fluorophenyl ester, HOBt ester, hydroxymethyl phosphine, O-methylisourea, DSC, NHS carbamate, glutaraldehyde, activated double bond, cyclic hemiacetal, NHS carbonate, imidazole carbamate, acyl imidazole, methylpyridinium ether, azlactone, cyanate ester, cyclic imidocarbonate, chlorotriazine, dehydroazepine, 6-sulfo-cytosine derivatives, maleimide, aziridine, TNB thiol, Ellman's reagent, peroxide, vinylsulfone, phenylthioester, diazoalkanes, diazoacetyl, epoxide, diazonium, benzophenone, anthraquinone, diazo derivatives, diazirine derivatives, psoralen derivatives, alkene, phenyl boronic acid, etc. In some embodiments, a first gRNA fragment comprises a first reactive group and the second gRNA fragment comprises a second reactive group. For example, the first and second reactive groups can each comprise an amine moiety, which are crosslinked with a carbonate-containing bifunctional crosslinking reagent to form a urea linkage. In other instances, (a) the first reactive group comprises a bromoacetyl moiety and the second reactive group comprises a sulfhydryl moiety, or (b) the first reactive group comprises a sulfhydryl moiety and the second reactive group comprises a bromoacetyl moiety, which are crosslinked by reacting the bromoacetyl moiety with the sulfhydryl moiety to form a bromoacetyl-thiol linkage. These and other cross-linking chemistries are known in the art, and are summarized in the literature, including by Greg T. Hermanson, Bioconjugate Techniques, 3rd Ed. 2013, published by Academic Press.

In some embodiments, the tracr is designed and/or modified according to embodiments described in International Application No. PCT/US17/69019 entitled "Synthetic guide molecules, compositions and methods relating thereto," the contents of which are hereby incorporated by reference in its entirety.

For example, a gRNA molecule can be described as:

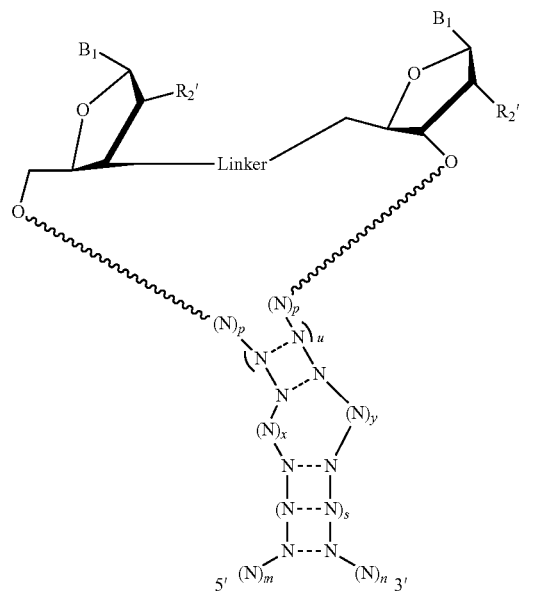

or

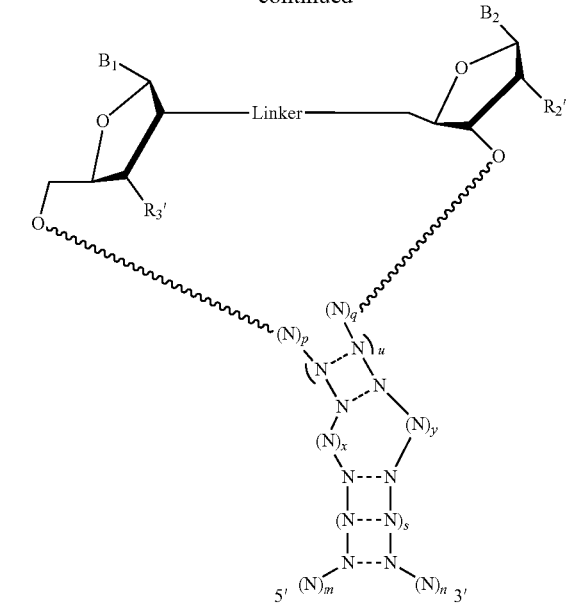

wherein:
each N is independently a nucleotide residue, optionally a modified nucleotide residue, each independently linked to its adjacent nucleotide(s) via a phosphodiester linkage, a phosphorothioate linkage, a phosphonoacetate linkage, a thiophosphonoacetate linkage, or a phosphoroamidate linkage; and
each N----N independently represents two complementary nucleotides, optionally two complementary nucleotides that are hydrogen bonding base-paired;
p and q are each 0;
u is an integer between 2 and 22, inclusive;
s is an integer between 1 and 10, inclusive;
x is an integer between 1 and 3, inclusive;
y is >x and an integer between 3 and 5, inclusive;
m is an integer 15 or greater; and
n is an integer 30 or greater.
In some embodiments, u is an integer between 2 and 22, inclusive;
s is an integer between 1 and 8, inclusive;
x is an integer between 1 and 3, inclusive;
y is >x and an integer between 3 and 5, inclusive;
m is an integer between 15 and 50, inclusive; and
n is an integer between 30 and 70, inclusive.
In some embodiments, the guide molecule does not comprise a tetraloop (p and q are each 0). In some embodiments, the lower stem sequence and the upper stem sequence do not comprise an identical sequence of more than 3 nucleotides.
In some embodiments, u is an integer between 3 and 22, inclusive.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g., complex with) a gRNA; and (b) together with the gRNA, associate with, and optionally cleave or modify, a target region of a DNA that includes (i)

a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity, etc.) of RNA-guided nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer. Cpf1, on the other hand, generally recognizes PAM sequences that are 5' of the protospacer.

In addition to recognizing specific sequential orientations of PAMs and protospacers, RNA-guided nucleases can also recognize specific PAM sequences. *S. aureus* Cas9, for instance, recognizes a PAM sequence of NNGRRT or NNGRRV, wherein the N residues are immediately 3' of the region recognized by the gRNA targeting domain. *S. pyogenes* Cas9 recognizes NGG PAM sequences. And *F. novicida* Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 ("Ran")), or that that do not cut at all.

Cas9

Crystal structures have been determined for *S. pyogenes* Cas9 (Jinek et al., Science 343(6176), 1247997, 2014 ("Jinek 2014"), and for *S. aureus* Cas9 in complex with a unimolecular guide RNA and a target DNA (Nishimasu 2014; Anders et al., Nature. 2014 Sep. 25; 513(7519):569-73 ("Anders 2014"); and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g., a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e., bottom) strand of the target nucleic acid. It may be formed from two or more split RuvC motifs (such as RuvC I, RuvCII, and RuvCIII in *S. pyogenes* and *S. aureus*). The HNH domain, meanwhile, is structurally similar to HNN endonuclease motifs, and cleaves the complementary (i.e., top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cpf1

The crystal structure of Acidaminococcus sp. Cpf1 in complex with crRNA and a dsDNA target including a TTTN PAM sequence has been solved by Yamano et al. (Cell. 2016 May 5; 165(4): 949-962 ("Yamano"), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Sequencing Methods

Methods of assessing compositions comprising guide RNA molecules are provided, which include determining the sequence of guide RNA molecules in a composition. Various methods of sequencing RNA molecules are known, which can be adapted for use according to the present disclosure. Generally, methods of the disclosure utilize certain nucleic acid polymerases that "template switch," using a first guide ribonucleic acid (gRNA) strand as a template for polymerization, and then switching to a second template nucleic acid strand (which may be referred to as a "template switching nucleic acid" or an "acceptor template") while continuing the polymerization reaction. The result is the synthesis of a hybrid nucleic acid strand with a 5' region complementary to the first template nucleic acid strand and a 3' region complementary to the template switching nucleic acid. In certain aspects, the nucleotide sequence of all or a portion (e.g., a 5' region) of the template switching oligonucleotide is predetermined such that the newly-synthesized hybrid nucleic acid strand includes a partial or complete sequence adapter at its 3' end useful for sequencing the hybrid nucleic acid strand using any sequencing platform. Such sequencing platforms include, but are not limited to, the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform of interest.

In certain aspects, the polymerization reaction is initiated using a primer that includes a partial or complete sequence adapter at its 5' end, resulting in a hybrid nucleic acid strand having a partial or complete sequence adapter at each end. The directionality of the adapters in the hybrid nucleic acid strand may be predetermined, e.g., by selecting the sequence adapter present at the 5' end of the primer, and the sequence adapter present at the 5' end of the template switching oligonucleotide. In some embodiments, the sequence adapter present in the primer and the sequence adapter in the template switching oligonucleotide are present at the 5' and 3' ends of the hybrid nucleic acid strand, respectively.

According to the methods of the present disclosure, reaction mixture components are combined under conditions sufficient to produce a product nucleic acid that includes the template gRNA and the template switching oligonucleotide, each hybridized to adjacent regions of a single product nucleic acid that includes a region polymerized from the dNTPs by the polymerase.

The reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent such as, but not limited to, sodium hydroxide, hydrochloric acid, phosphoric acid buffer solution, citric acid buffer solution, and the like. For example, the pH of the reaction mixture can be adjusted to a desired range by adding an appropriate amount of a pH adjusting agent. The temperature range suitable for production of a product nucleic acid may vary according to factors such as the particular polymerase employed, the melting temperatures of any optional primers employed, etc., and within the skill of one in the art. According to one embodiment, the polymerase is a reverse transcriptase (e.g., an MML V reverse transcriptase) and the reaction mixture conditions sufficient to produce the product nucleic acid include bringing the reaction mixture to a temperature ranging from 4° C. to 72° C., such as from 16° C. to 70° C., e.g., 37° C. to 50° C., such as 40° C. to 45° C., including 42° C. In another embodiment, the methods and systems described herein use a reverse transcriptases that operates at a temperature range, for example, a temperature range from about 55° C. to about 65° C. (e.g., 60° C.), or a temperature range from about 60° C. to about 70° C. (e.g., 65° C.). In another embodiment, the methods and systems described herein use a reverse transcriptase that operates at a temperature of about, for example, 42° C., 60° C., or 65° C. For example, the methods and systems described herein can use a TGIRT, which operates at a temperature of about 60° C. for about 5 min to about 60 min. As another example, the methods and systems described herein can use a Maxima RT, which operates at a temperature of about 65° C. for about 15 to about 30 minutes.

The template guide RNA may be of any type and length, and may include one or more modification, such as described herein. For example, a template gRNA may comprise from 5' to 3': a targeting domain (comprising a "core domain", and optionally a "secondary domain"); a first complementarity domain; a linking domain; a second complementarity domain; a proximal domain; and a tail domain. In some embodiments, the proximal domain and tail domain are taken together as a single domain. The targeting domain can include, e.g., 16, 17, 18, 19, 20, 21, 22, 23, 24, 25, or 26 nucleotides.

In an embodiment, a gRNA comprises a linking domain of no more than 25 nucleotides in length; a proximal and tail domain, that taken together, are at least 20 nucleotides in length; and a targeting domain of equal to or greater than 16, 17, 18, 19, 20, 21, 22, 23, 24, 25 or 26 nucleotides in length.

The gRNA sample that includes the template gRNA may be combined into the reaction mixture in an amount sufficient for producing a product nucleic acid. For example, the gRNA sample can be combined into the reaction mixture such that the final concentration of RNA in the reaction mixture is about 1 fg/µL to about 10 µg/µL, such as about 1 pg/µL to about 5 µg/µL, such as about 0.001 µg/µL, to about 2.5 µg/µL, such as about 0.005 µg/µL, to about 1 µg/µL, such as about 0.01 µg/µL to about 0.5 µg/µL, including about 0.1 µg/µL, to 0.25 µg/µL.

In some embodiments, one or more nucleotides are added to an end of the gRNA. For example, the gRNA can be a non-polyadenylated gRNA, and methods include adenylating (e.g., polyadenylating) the gRNA. Adenylating the gRNA may be performed using any convenient approach. In some embodiments, the adenylation is performed enzymatically, e.g., using Poly(A) polymerase or any other enzyme suitable for catalyzing the incorporation of adenine residues at the 3' terminus of the RNA.

Reaction mixtures for carrying out an adenylation reaction may include any useful components, including but not limited to, a polymerase, a buffer (e.g., a Tris-HCL buffer), one or more metal cations (e.g., $MgCl_2$, $MnCl_2$, or combinations thereof), a salt (e.g., NaCl), one or more enzyme-stabilizing components (e.g., OTT), ATP, and any other reaction components useful for facilitating the adenylation of a gRNA. The adenylation reaction may be carried out at a temperature (e.g., 30° C.-50° C., such as 37° C.) and pH (e.g., pH 7-pH 8.5, such as pH 7.9) compatible with the polymerase being employed, e.g., polyA polymerase. Other approaches for adding nucleotides to a gRNA include ligation-based strategies, where an gRNA ligase (e.g., T4 RNA ligase) catalyzes the covalent joining of a defined sequence to an end (e.g., the 3' end) of the gRNA to produce the template gRNA.

Methods of the present disclosure include combining a polymerase into the reaction mixture, which polymerase is capable of template switching, where the polymerase uses a first nucleic acid strand as a template for polymerization, and then switches to the 3' end of a second "acceptor" template nucleic acid strand to continue the same polymerization reaction. In certain aspects, the polymerase combined into the reaction mixture is a reverse transcriptase (RT). Reverse transcriptases capable of template-switching include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof. For example, the reverse transcriptase may be a Moloney Murine Leukemia Virus reverse transcriptase (MML V RT), a *Bombyx mori* reverse transcriptase (e.g., *Bombyx mori* R2 non-L TR element reverse transcriptase). Polymerases capable of template switching are commercially available and include SMARTScribe™ reverse transcriptase available from Clontech Laboratories, Inc. (Mountain View, Calif.), TGIRT™ reverse transcriptase available from InGex, LLC (St. Louis, Mo.), and Maxima reverse transcriptase available from Thermo Fisher Scientific Inc. In certain embodiments, a mix of two or more different polymerases is added to the reaction mixture, e.g., for improved processivity, proof-reading, and/or the like. In some instances, the polymer is one that is heterologous relative to the template, or source thereof. The polymerase is combined into the reaction mixture such that the final concentration of the polymerase is sufficient to produce a desired amount of a product nucleic acid. In certain aspects, the polymerase (e.g., a reverse transcriptase such as an MMLV RT or a *Bombyx mori* RT) is present in the reaction mixture at a final concentration of about 0.1 to about 200 units/µL (U/µL), such as about 0.5 to about 100 U/µL, such as about 1 to about 50 U/µL, including about 5 to about 25 U/µL, e.g., 20 U/µL.

In addition to a template switching capability, the polymerase combined into the reaction mixture may include other useful functionalities to facilitate production of a product nucleic acid. For example, the polymerase may have terminal transferase activity, where the polymerase is capable of catalyzing template-independent addition of deoxyribonucleotides to the 3' hydroxyl terminus of a DNA molecule. In certain embodiments, when the polymerase reaches the 5' end of the template gRNA, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent DNA strand. In certain embodiments, a polymerase having terminal transferase activity incorporates about 10 or fewer, such as about 5 or fewer (e.g., 3) additional nucleotides at the 3' end of the nascent DNA strand. All of the nucleotides may be the same (e.g., creating a homonucleotide stretch at the 3' end of the nascent strand) or at least one of the nucleotides may be different from the other(s). In certain embodiments, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). According to certain embodiments, the terminal transferase activity of the polymerase results in the addition of a homonucleotide stretch of 10 or less, such as 9, 8, 7, 6, 5, 4, 3, or 2 (e.g., 3) of the same nucleotides. For example, according to one embodiment, the polymerase is an MML V reverse transcriptase (MMLV RT) that incorporates additional nucleotides (predominantly dCTP, e.g., three dCTPs) at the 3' end of the nascent DNA strand. These additional nucleotides may be useful for enabling hybridization between the 3' end of the template switching oligonucleotide and the 3' end of the nascent DNA strand, e.g., to facilitate template switching by the polymerase from the template gRNA to the template switching oligonucleotide.

Methods of the disclosure include combining a template switching nucleic acid into a reaction mixture. In certain aspects, the template switching nucleic acid is a template switching oligonucleotide. By "template switching oligonucleotide" is meant an oligonucleotide template to which a polymerase switches from an initial template (e.g., a template gRNA) during a nucleic acid polymerization reaction. In such methods, the template gRNA may be referred to as a "donor template" and the template switching oligonucleotide may be referred to as an "acceptor template."

A reaction mixture includes the template switching oligonucleotide at a concentration sufficient to permit template switching of the polymerase from the template gRNA to the template switching oligonucleotide. For example, the template switching oligonucleotide may be added to the reaction mixture at a final concentration of about 0.01 to about 100 µM, e.g., about 0.1 to about 10 µM, about 0.5 to about 5 µM, about 1 to about 2 µM (e.g., 1.2 µM). The template switching oligonucleotide may include one or more nucleotides (or analogs thereof) that are modified or otherwise non-naturally occurring. For example, the template switching oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switching oligonucleotide.

The template switching oligonucleotide includes a 3' hybridization domain and a sequence adapter. The 3' hybridization domain may vary in length, and in some instances ranges from 2 to 10 nts in length, such as 3 to 7 nts in length. The sequence of the 3' hybridization may be any convenient sequence, e.g., an arbitrary sequence, a heteropolymeric sequence (e.g., a hetero-trinucleotide) or homopolymeric sequence (e.g., a homo-trinucleotide, such as G-G-G), or the like. Examples of 3' hybridization domains and template switching oligonucleotides are further described in U.S. Pat. No. 5,962,272 and Shiskin et al., Nat Methods. 12(4): 323-325 (2015). In addition to a 3' hybridization domain, the template switching oligonucleotide can include a sequence adapter. By "sequence adapter" is meant a nucleic acid construct that includes at least a portion of a nucleic acid domain (e.g., a sequence adapter nucleic acid sequence) utilized by a sequencing platform, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequence adapter includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; or any combination of such domains. In certain aspects, a barcode domain (e.g., sample index tag) and a molecular identification domain (e.g., a molecular index tag) may be included in the same nucleic acid.

The sequence adapters may include nucleic acid domains of any length and sequence suitable for the sequencing platform of interest. In certain embodiments, nucleic acid domains are about 4 to about 200 nucleotides in length. For example, the nucleic acid domains may be about 4 to about 100 nucleotides in length, e.g., about 6 to about 75, about 8 to about 50, about 10 to about 40, about 2 to about 8, about 9 to about 15, about 16 to about 22, about 23 to about 29, or about 30 to about 36 nucleotides in length.

The nucleic acid domains may have a length and sequence that enable a polynucleotide (e.g., an oligonucleotide) employed by a particular sequencing platform to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3'), P7 5'CAAGCAGAAGACGGCAT-ACGAGAT-3'), Read 1 primer (5'ACACTCTTTCCCTA-CACGACGCTCTTCCGATCT-3') and Read 2 primer (5'-GTGACTGGAGTTCAGACGTGTGCTCTTCCGATCT-3') domains employed on the Illumina®-based sequencing platforms. Other example nucleic acid domains include the A adapter (5'-CCATCT-CATCCCTGCGTGTCTCCGACTCAG-3') and P1 adapter (5'-CCTCTCTATGGGCAGTCGGTGAT-3') domains employed on the Ion Torrent™-based sequencing platforms. Sequence adapters are typically provided by a manufacturer of a sequencing platform (e.g., in technical documents provided with the sequencing system and/or available on the manufacturer's website). Based on such information, the sequence of a sequence adapter may be designed to include all or a portion of one or more nucleic acid domains in a configuration that enables sequencing the nucleic acid insert (corresponding to the template gRNA) on the platform of interest.

A template switching oligonucleotide may include a sequence (e.g., a defined nucleotide sequence 5' of the 3' hybridization domain of the template switching oligonucleotide), that enables second strand synthesis and/or PCR amplification of a single product nucleic acid. For example, the template switching oligonucleotide may include a sequence, where subsequent to generating the single product nucleic acid, second strand synthesis is performed using a primer that has that sequence. The second strand synthesis produces a second strand DNA complementary to the single product nucleic acid. Alternatively, or additionally, the single product nucleic acid may be amplified using a primer pair in which one of the primers has that sequence. Accordingly, in certain aspects, methods of the present disclosure may further include producing a product nucleic acid and contacting a 3' region of the single product nucleic acid complementary to the template switching oligonucleotide with a second strand primer configured to bind thereto under hybridization conditions. Following contacting the 3' region of the single product nucleic acid complementary to the template switching oligonucleotide with the second strand primer, methods may further include subjecting the reaction mixture to nucleic acid polymerization conditions.

A template switching oligonucleotide may, in some embodiments, include one or more of the following: (1) a 5' isomer nucleotides and/or a methylated deoxycytidine, (2) a unique molecular identifier (UMI), (3) a fixed four nucleotide barcode (or tag), and a (4) 3' ribonucleotide/locked nucleic acid (LNA). In certain embodiments, the fixed four nucleotide barcode is between the UMI and a 3' ribonucleotide/locked nucleic acid (LNA). In certain embodiments, a 5' isomer nucleotides and/or a methylated deoxycytidine can reduce concatenation because isomeric nucleotides do not pair with standard bases and methylation reduces the melting temperature. Moreover, in certain embodiments, a UMI provides for accurate counting of the number of gRNA molecules in a population, removes PCT under- and/or overrepresentation, and adds diversity ahead of the fixed four nucleotide barcode to improve sequencing quality. In certain embodiments, a fixed four nucleotide barcode removes ambiguities in determining if a nucleotide originates from the start of the gRNA molecule that begins with G or C nucleotide, or if it originates from the template-switching activity of the reverse transcriptase. Moreover, in certain embodiments, a 3' ribonucleotide/LNA improves base-pairing between the template switching oligonucleotide and the first cDNA strand. For example, the binding energy of the RNA-DNA complex can be greater than the binding energy of the LNA-DNA complex, which is also greater than the binding energy pf the DNA-DNA complex. In some embodiments, the template switching oligonucleotide is a template switching oligonucleotide described in Shishkin et al. (Shishkin, Giannoukos et al., Simultaneous gernation of many RNA-seq libraries in a single reaction, Nature Methods 2015), the contents of which is hereby incorporated by reference in its entirety. In some embodiments, the template switching oligonucleotide is 5'-/5Me-isodC//iisodG//iMe-iisodC/CTACACGACGCTCTTCC-GATCTNN NNNNNGCATrGrG-LNA(G)-3'.

Methods of the disclosure include combining dNTPs into the reaction mixture. In certain embodiments, each of the four naturally-occurring dNTPs (dATP, dGTP, dCTP and dTTP) are added to the reaction mixture. For example, dATP, dGTP, dCTP and dTTP are added to the reaction mixture such that the final concentration of each dNTP is about 0.01 to about 100 mM, e.g., about 0.1 to about 10 mM, about 0.5 to about 5 mM (e.g., 1 mM). At least one type of nucleotide added to the reaction mixture can be a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

In some embodiments, methods of the disclosure further include contacting the template gRNA with a first primer that primes the synthesis of a single product nucleic acid. The contacting is performed under conditions sufficient for the primer to hybridize to the template gRNA. The sequence of the primer can be arbitrary, e.g., the primer may be a random hexamer or any other random primer of suitable length (or mixtures thereof), or the primer can have a defined sequence, e.g., the primer sequence may be designed to specifically hybridize to a known complementary sequence in a template gRNA of interest (e.g., a polyA tail of the template gRNA).

In some embodiments, the primer includes two or more domains. For example, the primer may include a first (e.g., 3') domain that hybridizes to the template gRNA and a second (e.g., 5') domain that does not hybridize to the template gRNA. The sequence of the first and second domains may be independently defined or arbitrary. In certain embodiments, the first domain has a defined sequence and the sequence of the second domain is defined or arbitrary. In other embodiments, the first domain has an arbitrary sequence (e.g., a random sequence, such as a random hexamer sequence) and the sequence of the second domain is defined or arbitrary. In some embodiments, the second domain includes a nucleotide sequence that is the same as, or different from, a nucleotide sequence present in the template switching oligonucleotide. The second domain of the primer can include a sequence adapter, e.g., a sequence adapter described herein.

In some embodiments, the sequence adapter of the second domain of the primer is different from the sequence adapter of the template switching oligonucleotide. In some such embodiments, a single product nucleic acid (e.g., a cDNA or library thereof) can be produced with one end having one or more sequence adapters and the second end having one or more sequence adapters that are different from the first end. Having ends with different sequence adapters can be useful, e.g., for subsequent solid phase amplification (e.g., cluster generation using the surface-attached P5 and P7 primers in an Illumina®-based sequencing system), DNA sequencing (e.g., using the Read 1 and Read 2 primers in an Illumina®-based sequencing system), and any other steps performed by a sequencing platform requiring different sequence adapters at opposing ends of a nucleic acid to be sequenced. Having different ends is also useful in providing strand specific information, since the directionality of the sequenced strand is defined by the different ends.

In some methods, a template gRNA is contacted with a primer that includes one or more nucleotides (or analogs thereof) that are modified or otherwise non-naturally occurring. For example, the primer may include one or more nucleotide analogs (e.g., LNA, FANA, 2'-0-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the primer that primes the synthesis of the single product nucleic acid.

Any nucleic acids that find use in practicing the methods of the present disclosure (e.g., the template switching oligonucleotide, a primer that primes the synthesis of the single product nucleic acid, a second strand synthesis primer, one or more primers for amplifying the product nucleic acid, and/or the like) may include any useful nucleotide analogues and/or modifications, including any of the nucleotide analogues and/or modifications described herein. Once a product nucleic acid is produced, the methods may include inputting the product nucleic acid directly into a downstream application of interest (e.g., a sequencing application, etc.). In other aspects, methods may include using a product nucleic acid as a template for second-strand synthesis and/or PCR amplification (e.g., for subsequent sequencing of the amplicons). In some embodiments, methods of the present disclosure further include subjecting a product nucleic acid to nucleic acid amplification conditions. Such conditions may include the addition of forward and reverse primers configured to amplify all or a desired portion of the product nucleic acid, dNTPs, and a polymerase suitable for effecting the amplification (e.g., a thermostable polymerase). The single product nucleic acid may have an amplification sequence at its 5' end and an amplification sequence at its 3' end, and be subjected to PCR amplification conditions with primers complementary to the 5' and 3' amplification sequences. The amplification sequences may be (or overlap with) a nucleic acid domain in a sequence adapter, or may be outside of the sequence adapter. An initial step in carrying out amplification may include denaturing a product nucleic acid to dissociate the template gRNA and template switching oligonucleotide from the single product nucleic acid, thereby making the single product nucleic acid available for primer binding.

An exemplary method is shown in FIG. 1. As shown, a gRNA template is first polyadenylated at a 3' end. The method includes contacting the template gRNA with a first primer (e.g., a dT primer), which binds to the polyadenylated 3' end of the gRNA template and primes the synthesis of a first cDNA strand by a reverse transcriptase (RT), which adds a homo-trinucleotide (CCC) at the 3' end of the first cDNA strand. A template switching oligonucleotide ("TSO") is then added, which includes a homo-trinucleotide (GGG) at the 3' end that hybridizes to the CCC at the 3' end of the first cDNA strand. In the presence of the template switching oligonucleotide, the RT switches template and extends the first cDNA strand, producing a double-stranded "product nucleic acid" that includes the gRNA template (depicted in the top strand) and the extended first cDNA strand (i.e., a "single product nucleic acid", depicted in the bottom strand). As depicted, the product nucleic acid includes (i) the gRNA template, and (ii) the TSO, each hybridized to adjacent regions of the single product nucleic acid, which single product nucleic acid includes a region polymerized from dNTPs by the RT, which polymerized region is complementary to and hybridized to the 5' end of the gRNA template. The gRNA is then degraded to yield only the single product nucleic acid, which serves as a template for a 1$^{st}$ dsDNA. Forward and reverse PCR primers with adapters in combination with the 1$^{st}$ dsDNA are then exposed to conditions sufficient to undergo PCR amplification. A total of 8 cycles are used in this exemplary method to amplify a dsDNA product that includes a complete set of sequence adapters for sequencing.

The method steps and components depicted in FIG. 1 are exemplary, and any depicted method step or component can be modified to include any method step or component described herein (e.g., primers, template switching oligonucleotides, reverse transcriptases, etc.).

Implementation of Genome Editing Systems:
Delivery, Formulations, and Routes of
Administration Genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 2 and 3 set forth several, non-limiting examples of genome editing system implementations. Those of skill in the art will appreciate, however, that these listings are not comprehensive, and that other implementations may be possible. With reference to Table 2 in particular, the table lists several exemplary implementations of a genome editing system comprising a single gRNA and an optional donor template. However, genome editing systems according to this disclosure may incorporate multiple gRNAs, multiple RNA-guided nucleases, and other components such as proteins, and a variety of implementations will be evident to the skilled artisan based on the principles illustrated in Table 2. In Table 2, "[N/A]" indicates that the genome editing system does not include the indicated component.

TABLE 2

Genome Editing System Components

| RNA-guided Nuclease | gRNA | Donor Template | Comments |
|---|---|---|---|
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | | DNA | An RNA-guided nuclease protein and a single DNA encoding both a gRNA and a donor template. |
| | | DNA | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | | DNA | A first DNA or DNA vector encoding an RNA-guided nuclease and second DNA or DNA vector encoding a gRNA and a donor template. |
| DNA | DNA | | A first DNA or DNA vector encoding an RNA-guided nuclease and a donor template, and a second DNA or DNA vector encoding a gRNA |
| DNA | RNA | | A DNA or DNA vector encoding an RNA-guided nuclease and a donor template, and a gRNA |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 3 summarizes various delivery methods for the components of genome editing systems, as described herein. Again, the listing is intended to be exemplary rather than limiting.

TABLE 3

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |

TABLE 3-continued

| Delivery Vector/Mode | Delivery into Non-Dividing Cells | Duration of Expression | Genome Integration | Type of Molecule Delivered |
|---|---|---|---|---|
| Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or may be conjugated to molecules (e.g., N-acetylgalactosamine) promoting uptake by the target cells (e.g., erythrocytes, HSCs). Nucleic acid vectors, such as the vectors summarized in Table 3, may also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g. inserted into, fused to) a sequence coding for a protein. As one example, a nucleic acid vectors can include a Cas9 coding sequence that includes one or more nuclear localization sequences (e.g., from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 3, and additional suitable viral vectors and their use and production are described in Cotta-Ramusino. Other viral vectors known in the art may also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which may be organic or inorganic. Nanoparticles are well known in the art, and are summarized in Cotta-Ramusino. Any suitable nanoparticle design may be used to deliver genome editing system components or nucleic acids encoding such components. For instance, organic (e.g. lipid and/or polymer) nonparticles may be suitable for use as delivery vehicles in certain embodiments of this disclosure. Exemplary lipids for use in nanoparticle formulations, and/or gene transfer are shown in Table 4, and Table 5 lists exemplary polymers for use in gene transfer and/or nanoparticle formulations.

TABLE 4

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |

TABLE 4-continued

Lipids Used for Gene Transfer

| Lipid | Abbreviation | Feature |
|---|---|---|
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 5

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]R-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In an embodiment, the nucleic acid molecule is delivered at the same time as one or more of the components of the Genome editing system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In an embodiment, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease-molecule component and/or the gRNA component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, may also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol may be used in connection with the various embodiments of this disclosure.

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically may be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In an embodiment, significantly smaller amounts of the components (compared with systemic approaches) may exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration may be provided as a periodic bolus (for example, intravenously) or as continuous infusion from an internal reservoir or from an external reservoir (for example, from an intravenous bag or implantable pump). Components may be administered locally, for example, by continuous release from a sustained release drug delivery device.

In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate that different components of genome editing systems can be delivered together or separately and simultaneously or nonsimultaneously. Separate and/or asynchronous delivery of genome editing system components may be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In an embodiment, a gRNA can be delivered by such modes. The RNA-guided nuclease molecule component can be delivered by a mode which results in less persistence or less exposure to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or exposure.

In certain embodiments, the second mode of delivery is selected to optimize, e.g., maximize, a pharmacodynamic or pharmacokinetic property, e.g., distribution, persistence or exposure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA is delivered by a first delivery mode that results in a first spatial, e.g., tissue, distribution: A second component, e.g., a RNA-guided nuclease molecule is delivered by a second delivery mode that results in a second spatial, e.g., tissue, distribution. In an embodiment the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

All publications, patent applications, patents, and other references mentioned herein are incorporated by reference in their entirety. In addition, the materials, methods, and examples are illustrative only and not intended to be limiting. The disclosure is further illustrated by the following example. The example is provided for illustrative purposes only. It is not to be construed as limiting the scope or content of the disclosure in any way.

EXAMPLE

Example 1: Template-Switching Next-Generation Sequencing (NGS) Assay for Quality Control (QC) of gRNAs The present Example describes methods of using a NGS assay for generation of robust products from a relatively small amount of input material (e.g., 50 ng). The present Example also describes methods for assessing and differentiating quality of synthetic gRNAs produced by a variety of out sourced and in-house methods. Moreover, the present Example shows that gRNAs having a variety of linkage chemistries and end-modifications are compatible with the described methods. Further, the present Example describes evaluation and/or validation of poor performing gRNAs, and can, in turn, determine if poor performance is due to the gRNA targeting sequencing (or not). Furthermore, the present Example validates both inter- and intra-assay sensitivity. Accordingly, the present Example, among other things, demonstrates that methods of the present disclosure are sufficiently sensitive to distinguish quality of multiple samples of gRNAs, such as outsourced and in-house gRNA products and assess lot-to-lot quality.

Methods and Materials

Synthetic gRNAs Having a Predetermined Sequence

In this example, synthetic gRNAs having a predetermined gRNA sequence, were validated by the methods described herein.

PCR Methods

For the present Example, a Moloney Murine Leukemia Virus (MMLV)-derived transcriptase (RT) was used to synthesize cDNA from gRNA templates. MMLV-RT is an RNA-dependent DNA polymerase that can be used in cDNA synthesis with long messenger RNA templates (greater than 5 kb). The template switching activity of MMLV-RT adds a second primer that allows reading of a cDNA sequence, and can generate high yield of cDNA from low gRNA input (e.g., 50 ng).

In this Example, a template-switching NGS assay for QC of gRNAs was developed to assess the 5' sequence integrity of the gRNA sequence (FIG. 1). FIG. 1 depicts a method for assessing quality control metrics of a pool (or, in other embodiments, a library) of gRNAs (modified for gRNAs from "SMARTer smRNA Kit for Illumina-Sequence Small RNAs with High Sensitivity and Minimal Bias" (available at http://www.clontech.com/US/Products/cDNA_Synthesis_and_Library_Construction/Next_Gen Sequencing_Kits/smRNA-Seq, the contents of which are hereby incorporated by reference in its entirety). The Clontech kit is designed to add a poly(A) tail to RNAs. The poly(A) tail added to RNAs allows subsequent annealing of the dT primer ahead of reverse transcription.

The current method allows sequencing of gRNAs that possess a poly(A) tail (e.g., tailed synthetic or IVT gRNAs). For example, in the methods described herein, the polyadenylation step was removed from the Clontech kit by discarding the Poly(A) polymerase and performing a room temperature incubation in the presence of RNase inhibitor and ATP in lieu of the standard polyadenylation step. One advantage of removing the polyadenylation step is that there is a reduction in variability associated with this step (e.g., number of As added), thereby potentially improving analysis of the 3' end.

Moreover, the extension step of the PCR protocol described herein is quite different than the extension step provided by the Clontech kit. For example, the extension step has been increased from 10 sec as suggested in the kit to 30 sec. This increase in time was chosen in consideration of the length of the gRNAs that was used for analysis. As another example, methods described herein included a targeted extension reaction. For instance, in contrast to priming from the poly(A) tail, a custom primer with an Illumina tail targeting a TRACR sequence (5'-GTGACTGGAGTTCAGACGTGTGCTCTTCC-GATCTNNNNNNNNNNTCAGTTTTTCAAG TTGATAACGGTC-3') can be used.

Moreover, the Clontech protocol recommends size selection post-PCR using either BluePippin or SPRI bead protocols. By contrast, the provided methods described herein use both steps: a size selection with BluePippin followed by SPRI treatment to further clean up the sample.

gRNAs analyzed according to the provided methods comprise one of two formats: those with a pre-existing poly(A) tail, and those that required addition of a poly(A) tail. For the latter, the addition of a tail was accomplished by incubation of gRNA with poly(A) polymerase in the presence of RNase inhibitor and ATP for 5 minutes at 16° C. For gRNAs that had a pre-existing poly(A) tail, gRNA was incubated for 5 minutes at room temperature in the presence of RNase inhibitor and ATP, but in the absence of Poly(A) polymerase. Following these steps, both gRNA format types contained a poly(A) tail.

Primer (e.g., dT primer or alternative primer) was then annealed to the tailed gRNA at 72° C. over 3 minutes. First-strand cDNA was synthesized by addition of reverse transcriptase and template-switching oligonucleotide (TSO), with reactions carried out for 60 minutes at 42° C. in the presence of RNase inhibitor. gRNA template was then degraded at 70° C. for 10 minutes, leaving a first-strand cDNA template for PCR amplification. PCR was carried using the following program: initial denaturation at 98° C. for 1 minute; 8 cycles of denaturation (98° C. for 10 seconds), annealing (60° C. for 5 seconds), and extension (68° C. for 30 seconds); and a holding step at 4° C.

The PCR product was purified from components of the enzymatic reaction using the NucleoSpin Gel and PCR Clean-Up kit (https://protect-us.mimecast.com/s/EJqNB0IYKa6i7). Following cleanup, PCR products from individual gRNA were assessed with QC methods such as electrophoresis (e.g., BioA) and fluorometric quantitation (e.g., Qubit). Individual PCR products that passed QC were pooled, and the resulting pooled fraction was size selected (e.g., for 150-300 bp fragments) using the BluePippin size selection system (https://protect-us.mimecast.com/s/RKxWB0S6rLVUM) to create a library for sequencing. A final SPRI bead-based cleanup/concentration (https://protect-us.mimecast.com/s/v13eBzU2MG8fE) and round of QC (e.g., BioA and/or Qubit) was performed on this library. Provided that this final QC was passed, the library was then sent for NGS and downstream analysis.

Computational Analysis for gRNA Quality Control (QC) by Next-Generation Sequencing (NGS)

The present Example also provides for systems and methods for computation analysis for gRNA QC by NGS. In particular the present Example provides systems and methods for assessing and/or determining the targeting sequence (e.g., a 5' end targeting sequence) of a sample of gRNAs, according to various embodiments of the invention.

For example, the first step for data analysis involved aligning each sequencing read to a reference sequence. This step was followed by classifying and quantifying any bases from the read that did not align perfectly to the reference (e.g., any bases that are considered mismatches or indels/gaps by the alignment algorithm). Sequencing reads that were highly divergent from the expected reference sequence and/or had low quality were classified as contaminants or artifacts and filtered out from the final quality control statistics.

The reference sequence for alignment was generated by concatenating the nucleotides expected to be incorporated by the template switching reverse transcriptase (RT) and the guide RNA (gRNA) sequence, including the spacer and tracr portions. In this context, the gRNA sequence was specified with thymine (T) characters replacing uracil (U) characters, because the sequenced molecule is the corresponding cDNA, rather than the gRNA itself. An example reference sequence is: 5'-[G/C][G/C][G/C] [spacer sequence] [tracr sequence]-3', where adjacent square brackets imply concatenation of the DNA sequences and slashes indicate partially ambiguous nucleotide characters. However, the reference sequence can also be created with an undetermined base character (N) to represent the bases incorporated at the 5' end. Alternatively, if the gRNA sequence is not known in advance, it can be inferred from the sequencing data by identifying the most abundant read sequence for a given sample and using it as a reference. In this example, the bases at the 5' end can be altered to reflect the stochasticity in base incorporation of the template switching reverse transcriptase (RT).

The frequency with which individual bases and length variances occur at each position from the 5' end of the molecule between a given read and the reference sequence was performed using the Needleman-Wunsch algorithm, although other global algorithms can be similarly used. At each position in the reference sequence, the identity of the base from the read sequence aligned to that position was determined and used to generate a frequency table describing how often each base occurred at a given position. Bases in the read that differed from the expected reference sequence were counted as substitution errors. If the alignment contained a gap character (or indel) in the reference sequence, it was counted as an inserted base in the read occurring at the position where the gap occurred. If the gap character occurred in the read sequence, it was counted as a deletion in the gRNA sequence at the corresponding alignment position in the reference sequence. The number of total reads that did not contain any mismatches relative to the reference sequence was also tracked and reported as a quality control metric.

In a parallel method, reads that did not align closely to the expected reference sequence were removed from the analysis process, as they may be derived from contaminants or be caused by experimental or sequencing artifacts. This filtering was achieved by removing reads that had a large number of base differences relative to the reference sequence (for example, greater than 15% bases in the read did not match those in the reference sequence). Reads were also be filtered using the quality scores provided by the sequencing instrument and associated software (for example, requiring mean and median Phred score across the length of the read to be greater than 35). These filtering approaches were used simultaneously to avoid counting reads that did not represent accurate representations of the guide RNA molecules being analyzed.

Results

FIGS. 2A-2C depict data of generation of robust dsDNA products from low input material. A BioAnalyzer (BioA) instrument provided automated gel electrophoresis and laser-induced fluorescence to help serve as quality control (QC) for dsDNA PCR products generated from reverse transcription of gRNA. Adapter sequences added 153 bp to RNA-derived sequences (Expected size=~250 bp (97-100mer+153 bp)). Main peaks shown in FIGS. 2A-2C indicated a desired product. These figures demonstrated that robust products were achieved with 50 ng (~2 µmol) gRNA.

Figure 3A:
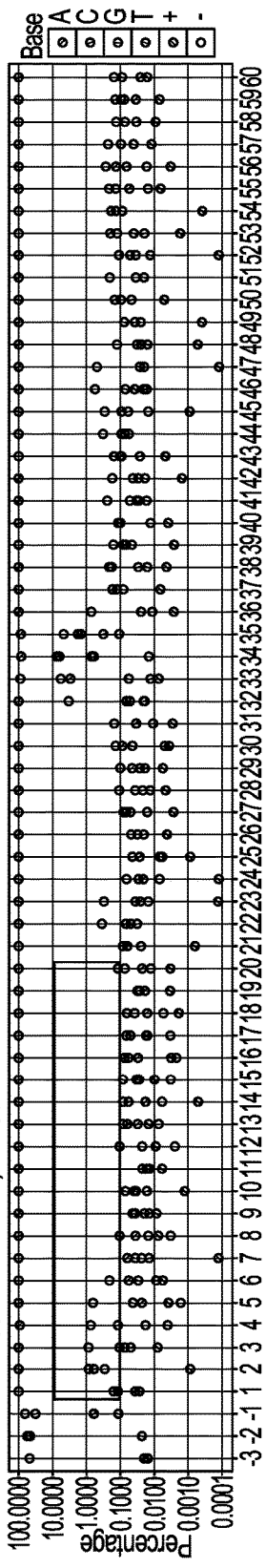
FIGS. 3A-3C are plots depicting the frequency with which individual bases (A, G, C, T) and length variances (+,−) occur at each position from the 5' end of the complementary DNAs (cDNAs) generated from synthesized gRNAs. Red boxes indicate the 20 bp targeting sequence of the gRNA; positions to the left of the boxes are added during cDNA synthesis and are not part of the gRNA. Sequencing was performed after 150-300 bp size selection. Note that the sequence in FIG. 3C is a different sequence than the sequences in FIGS. 3A and 3B.
Figure 3B:
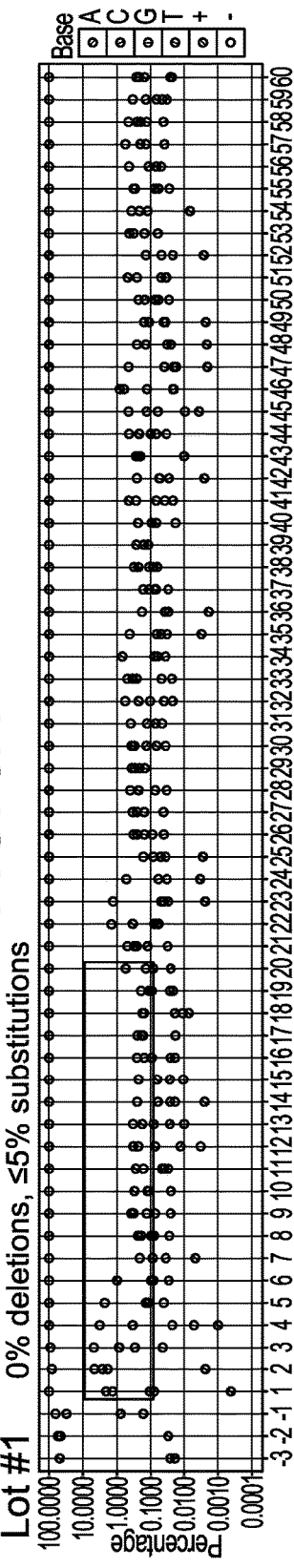
Figure 3C:
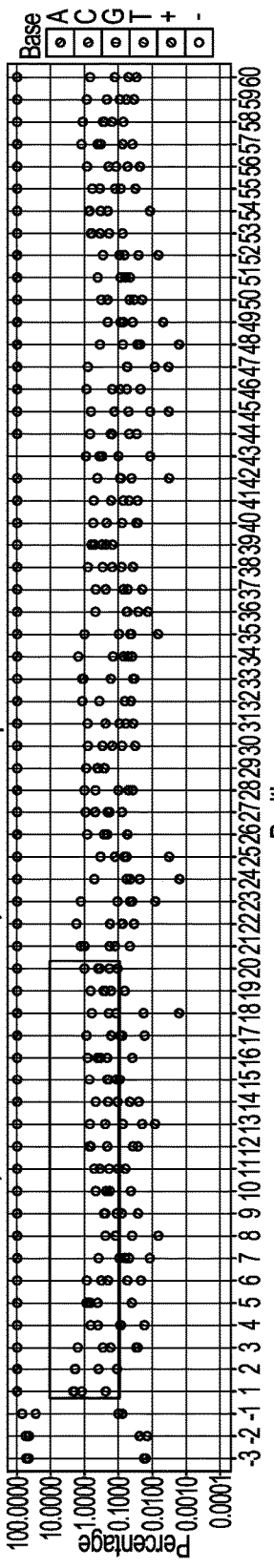

As described herein, conventional mass spectrometry methods for assessing gRNA quality suffers from low specificity and, accordingly, fails to identify contaminates in a gRNA Lot. FIGS. 3A-3C are plots depicting the frequency with which individual bases and length variances occur at each position from the 5' end of the molecule. FIGS. 3A-3C show the degree of sequence variation observed in three separate gRNA samples. The red box delineates rates of variation between 1 and 10% across the 20 bp targeting sequence of each gRNA sample. Sequence analysis was performed after 150-300 bp size selection.

All gRNAs used in this example were based on a predetermined gRNA sequence, and were validated by the methods described herein. In this example, synthetic gRNAs from Lot #2 resulted in greater sequence fidelity in target region compared to the synthetic gRNAs from Lot #1 and Lot #3. Furthermore, the methods described herein revealed that the gRNA sequence from Lot #3 was in fact not the predetermined sequence as expected (FIG. 3C).

In the samples synthesized according to the methods disclosed herein, fewer than 1% of sequencing reads revealed changes in base identity of sequence length across the first 20 positions of the gRNA, starting from the 5' end. A slight increase in variances were observed at positions 32 through 35 in gRNAs synthesized by the methods described herein; these positions correspond to the cross-linker bridging the first and second gRNA fragments, and indicate that gRNAs incorporating such cross-linkers can serve as substrates for cDNA synthesis and, consequently, can be subjected to sequencing and to sequence fidelity assays. By contrast, in the synthetic gRNA samples, fewer than 10% of reads revealed changes in base identity, and fewer than 5% revealed changes in sequence length across the 20 bases at the 5' end of the gRNA.

Therefore, the results that are shown in FIGS. 3A-3C reveal that the methods described herein, in contrast to other conventional methods, provide the ability to identify samples and sites were a degree of sequence variation is unacceptably high.

Figure 4A:
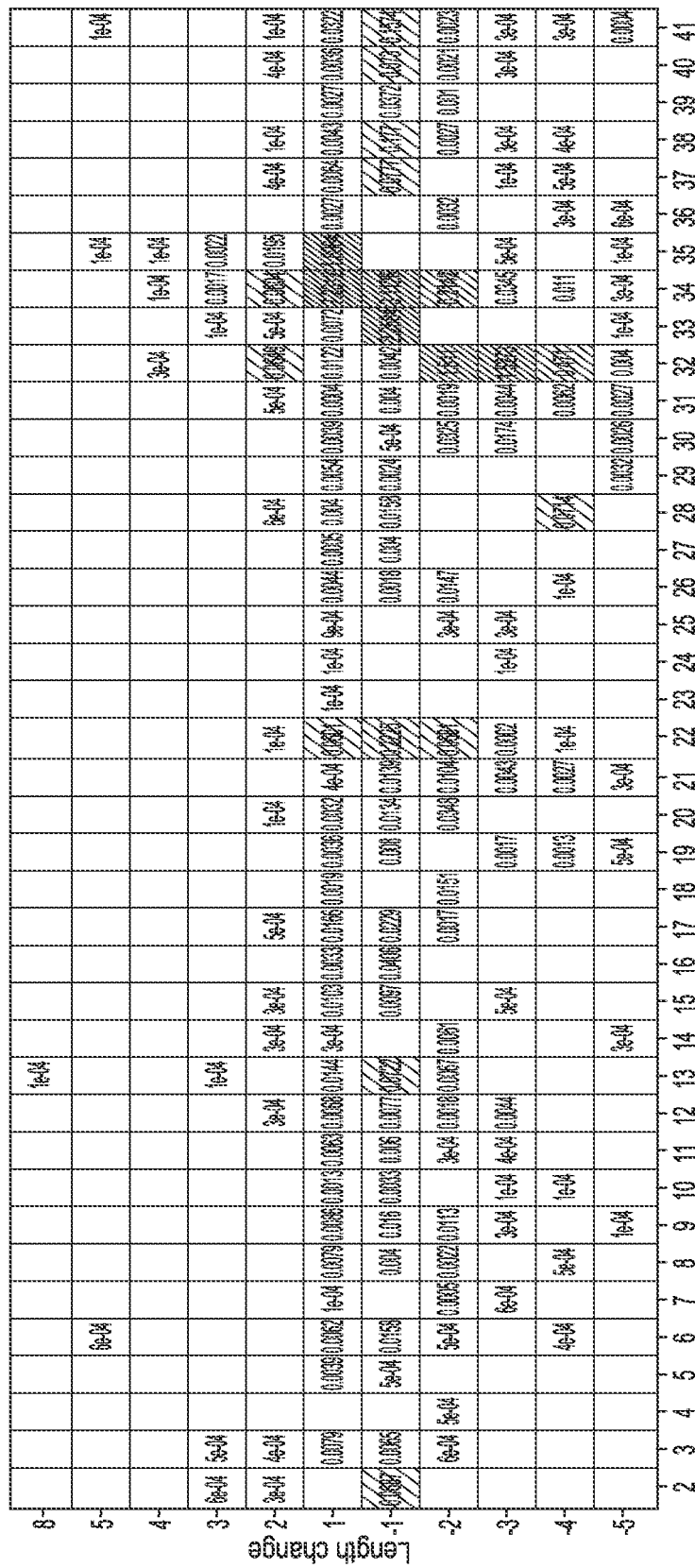
FIGS. 4A-4C are graphs depicting internal sequence length variances at the first 41 positions from the 5' ends of cDNAs generated from various synthetic gRNA compositions, relative to a reference sequence.
Figure 4B:
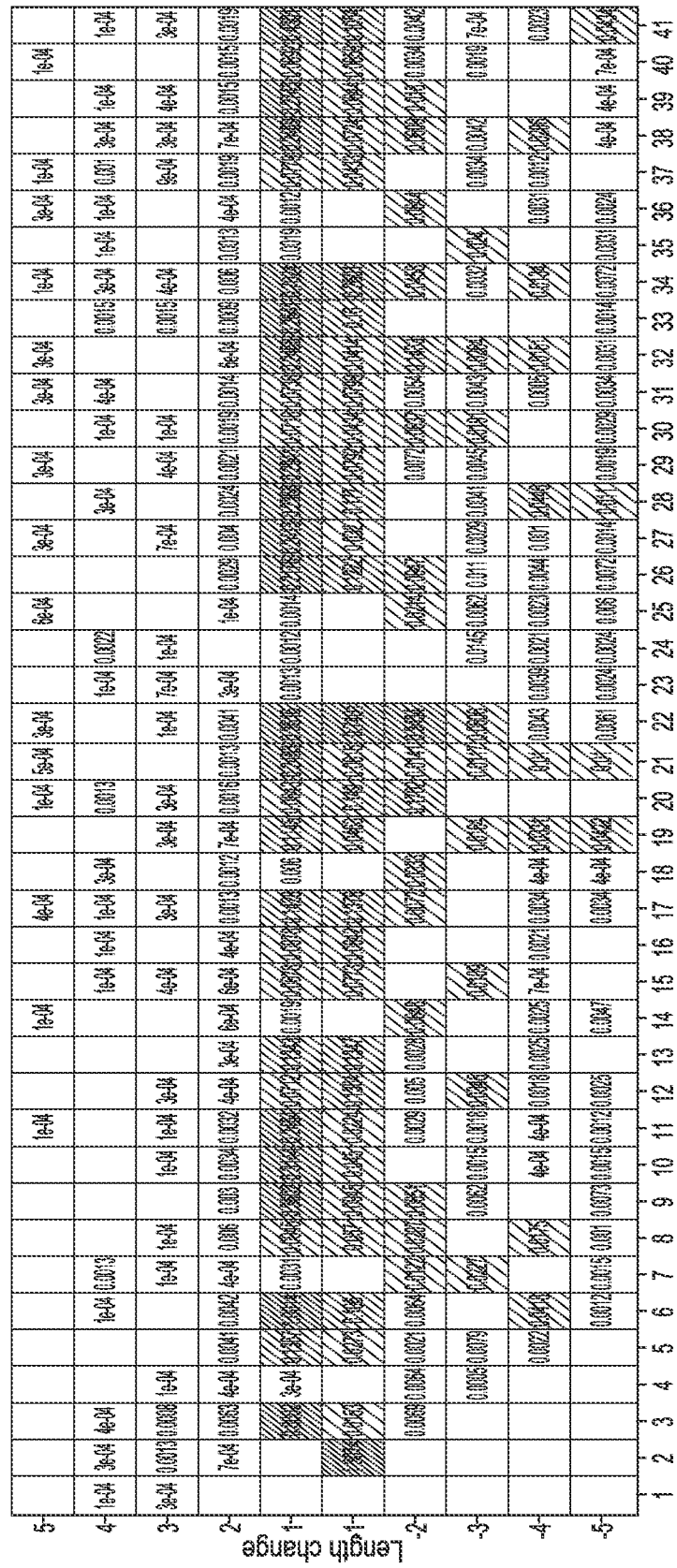
Figure 4C:
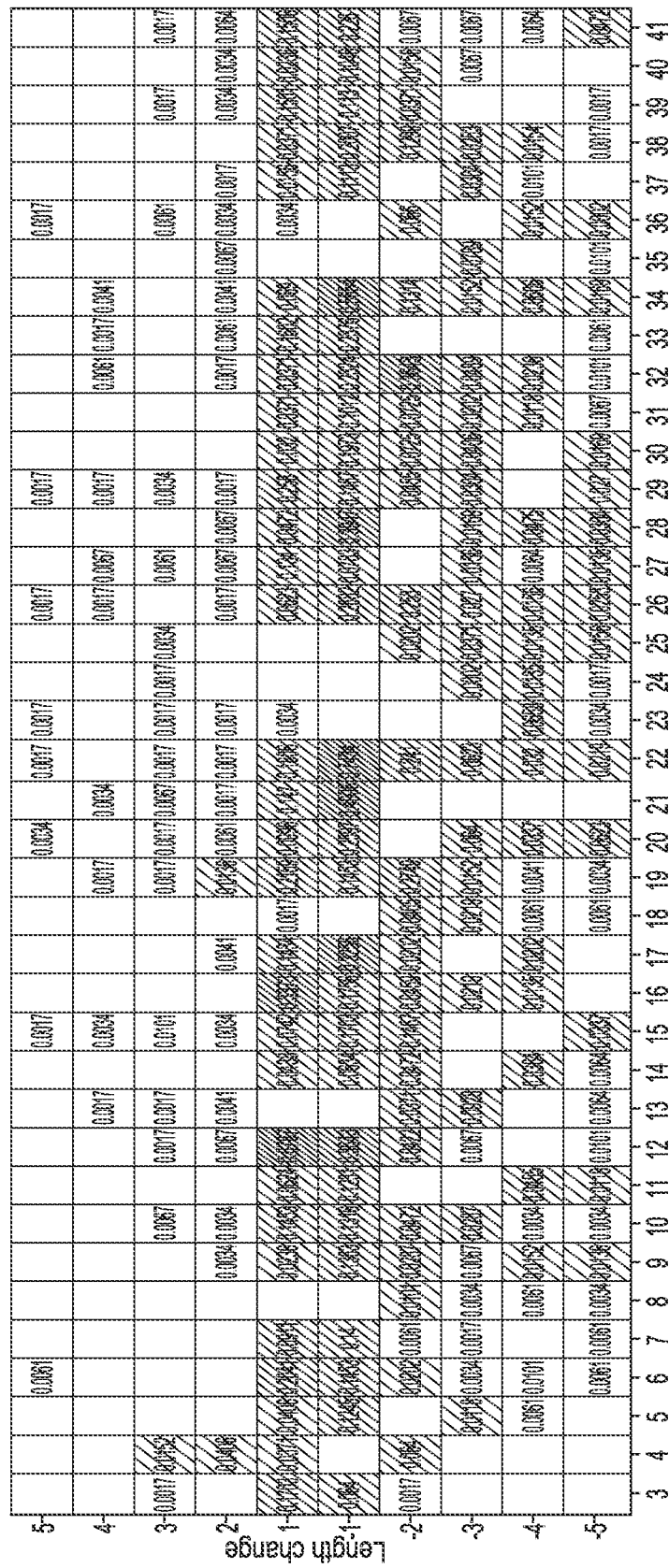
Figure 5A:
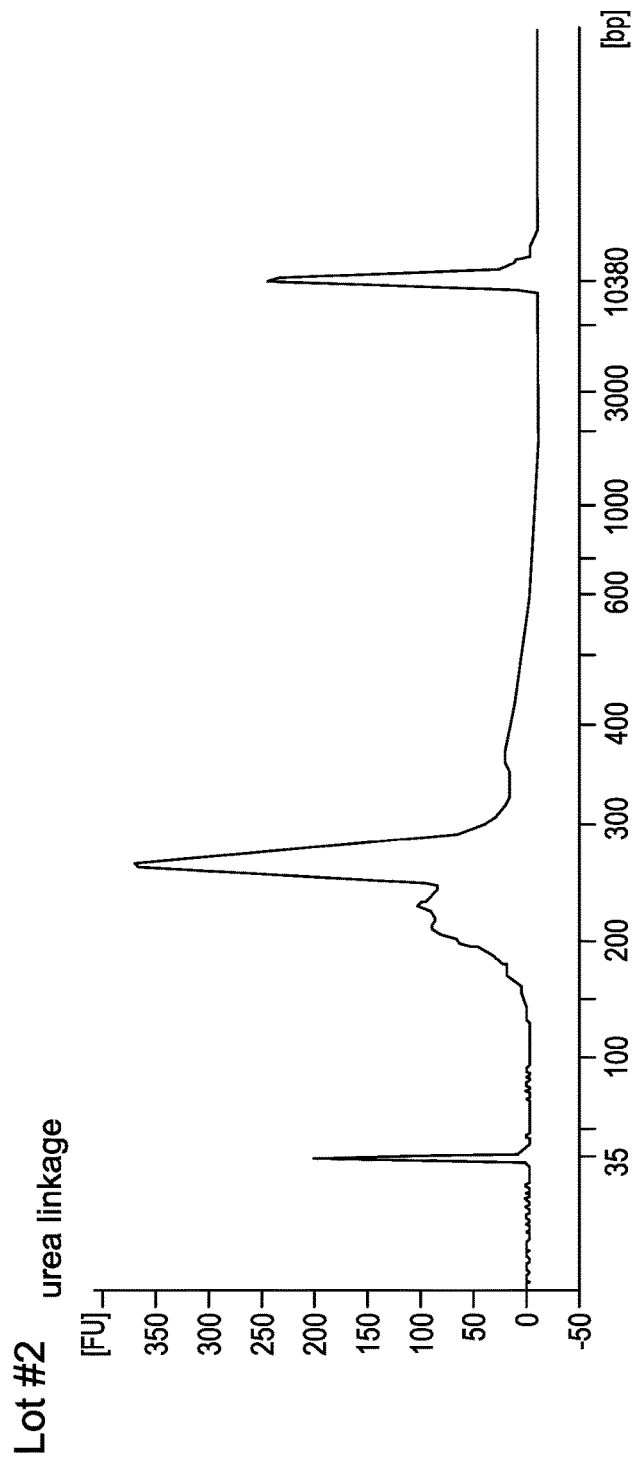
FIG. 5A is a BioAnalyzer (BioA) electrophoretic trace for dsDNA PCR products generated from reverse transcription of a sample of gRNAs that include a urea linkage.
Figure 5B:
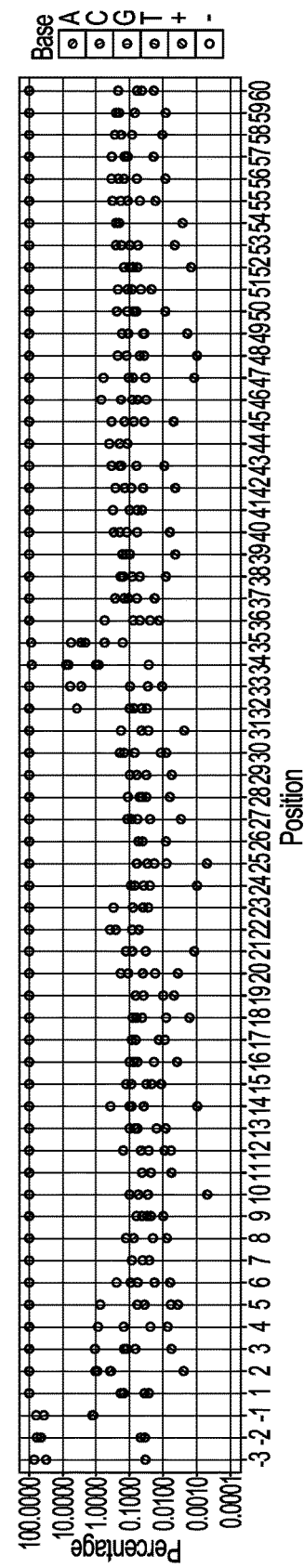
FIG. 5B shows a plot depicting the frequency with which individual bases and length variances occur at each position corresponding to the 5' end of the gRNAs.
Figure 5C:
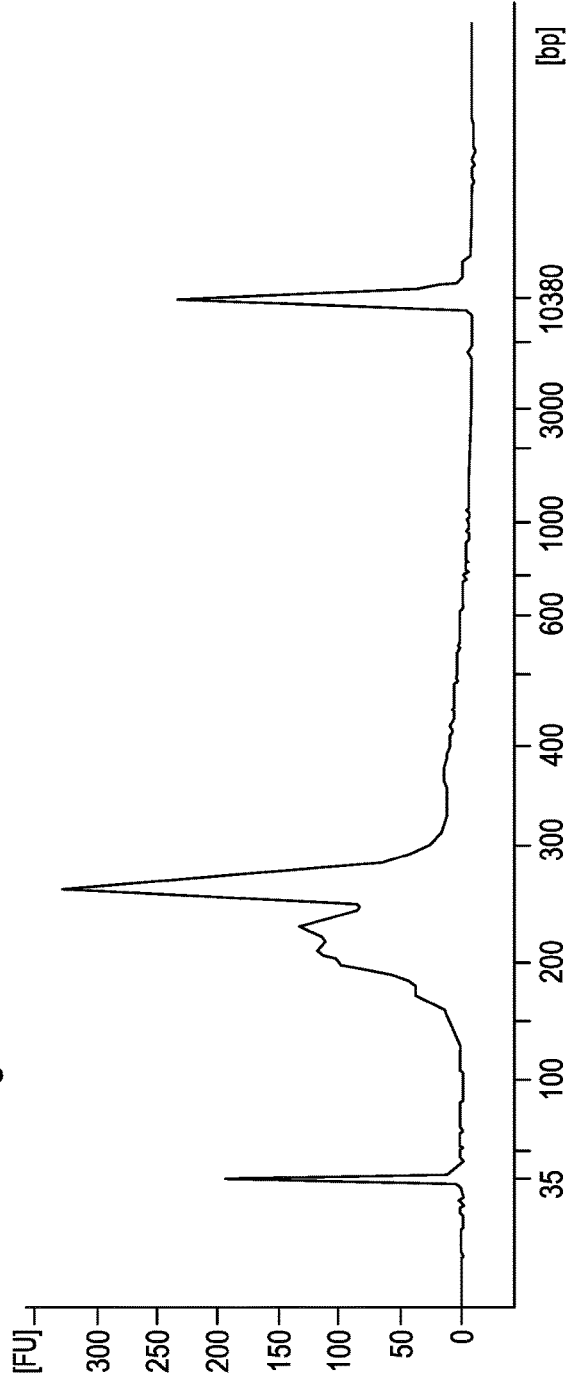
FIG. 5C is a BioAnalyzer (BioA) electrophoretic trace for dsDNA PCR products generated from reverse transcription of a sample of gRNAs that include a bromothiol linkage.
Figure 5D:
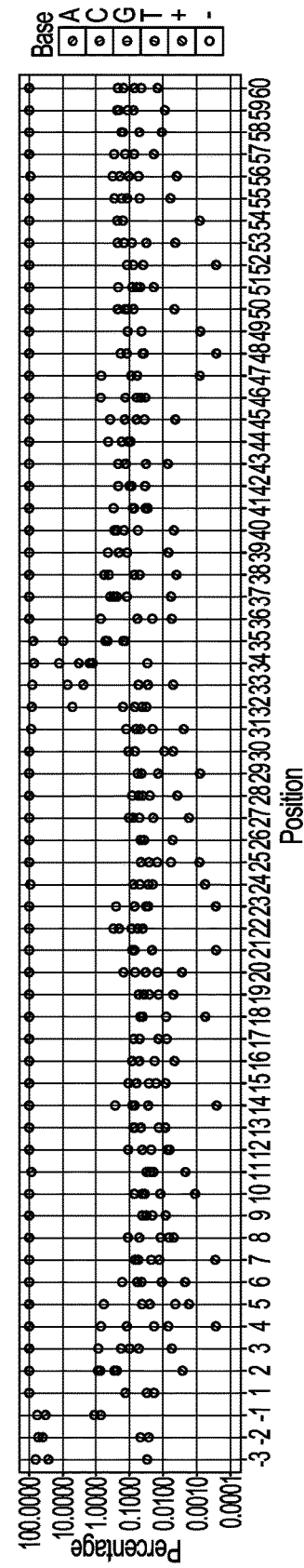
FIG. 5D shows a plot depicting the frequency with which individual bases and length variances occur at each position corresponding to the 5' end of the molecule of a sample of gRNAs that include a bromothiol linkage.

FIGS. 4A-4C depict graphs showing internal sequence length variances at the first 41 positions from the 5' end of various synthetic gRNA compositions of gRNA preparations, relative to a reference sequence. The results in FIGS. 4A-4C show that Lot #2 (FIG. 4A) exhibited less frequent sequence length variances compared to the synthetic gRNA sequences from Lot #1 (FIG. 4B) and Lot #2 (FIG. 4C). Notably, the graph shown in FIG. 4A indicates that the gRNA targeting sequences from Lot #2 harbored minimal sequence length variance compared to the gRNA targeting sequences from Lot #1 (FIG. 4B) and Lot #2 (FIG. 4C). These results would be helpful, for example, when determining a lot of gRNA sequences to use that would reduce off-targeting effects.

The figures show the frequency of internal length variances is very low across the first 20 positions from the 5' terminus among the gRNA molecules, though increased variances are observed in the vicinity of the cross-linker. However, in one of the lot samples, sequence length variances are observed at a higher frequency within the first 20 positions of the 5' end of the gRNA.

FIGS. 5A-5D show that the methods can be adapted for the assessment of gRNAs incorporating non-nucleic acid components, such as synthetic cross-linkers. In this example, 5' sequence fidelity was measured in two-part synthetic gRNAs comprising a non-nucleic acid (e.g., urea linkage, e.g., bromothiol linkage). This assay showed a region of relatively high frequency of mismatches/indels at linkage site (position 34), which is information that cannot be achieved by using other methods (e.g., mass spectroscopy methods). This assay confirmed that reverse transcription is likely affected at linkage site, and that the assay detected presence of linkage.

Figure 6A:
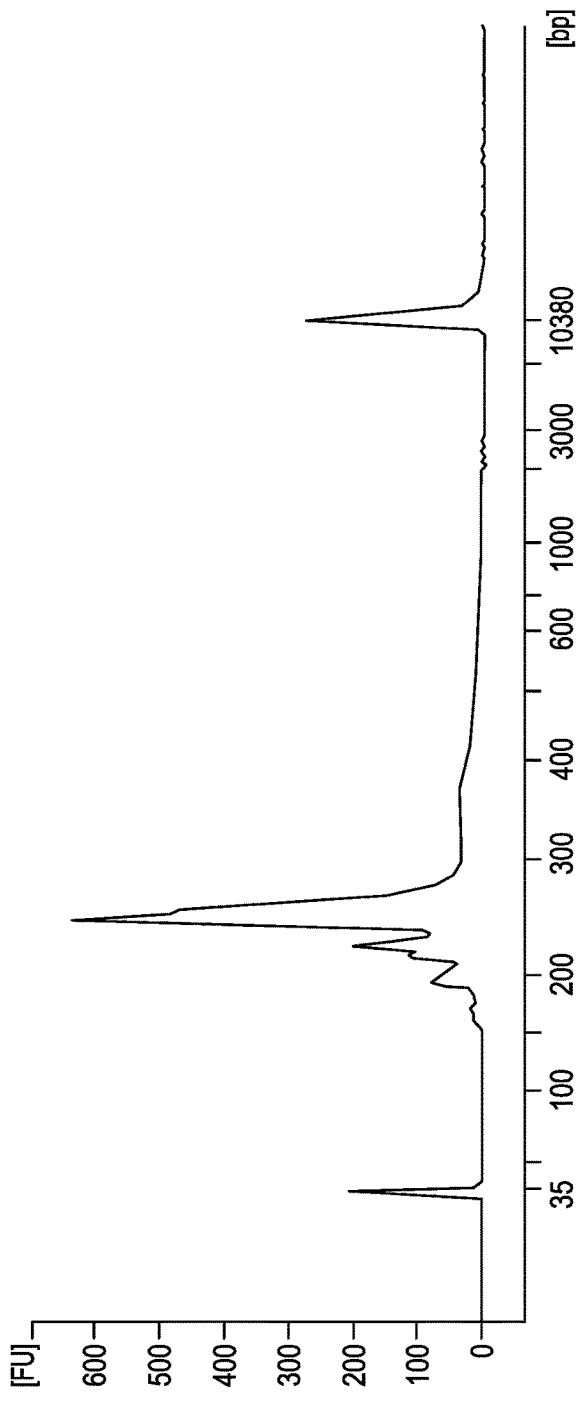
FIG. 6A is a BioAnalyzer (BioA) electrophoretic trace for dsDNA PCR products generated from reverse transcription of a sample of gRNAs that include a 5' ARCA cap and include 3' polyadenylation.
Figure 6B:
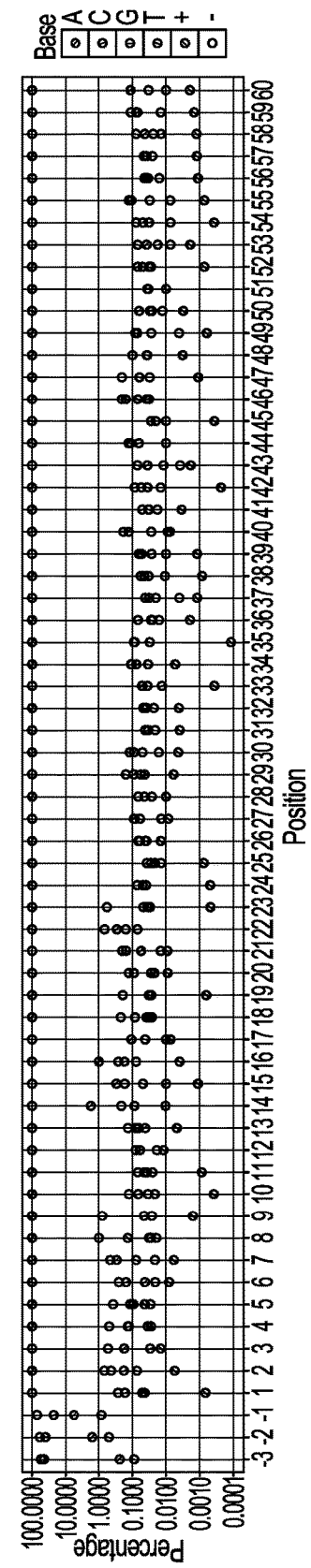
FIG. 6B is a plot depicting the frequency with which individual bases and length variances occur at each position from the 5' end of the molecule that includes a 5' ARCA cap and include 3' polyadenylation to a reference sequence.

FIGS. 6A-6B depict that the provided methods are compatible with chemical end-modifications. In this example, an assay was run on ARCA-capped, polyadenylated gRNA. Accordingly, the polyadenylation step, for example, as provided in FIG. 1, was removed. FIG. 6B depicts that the provided methods are capable of measure 5' sequence fidelity of a capped guide, and that the provided methods can be simplified via removal of polyadenylation step when evaluating gRNAs having p(A) tails.

Figure 7A:
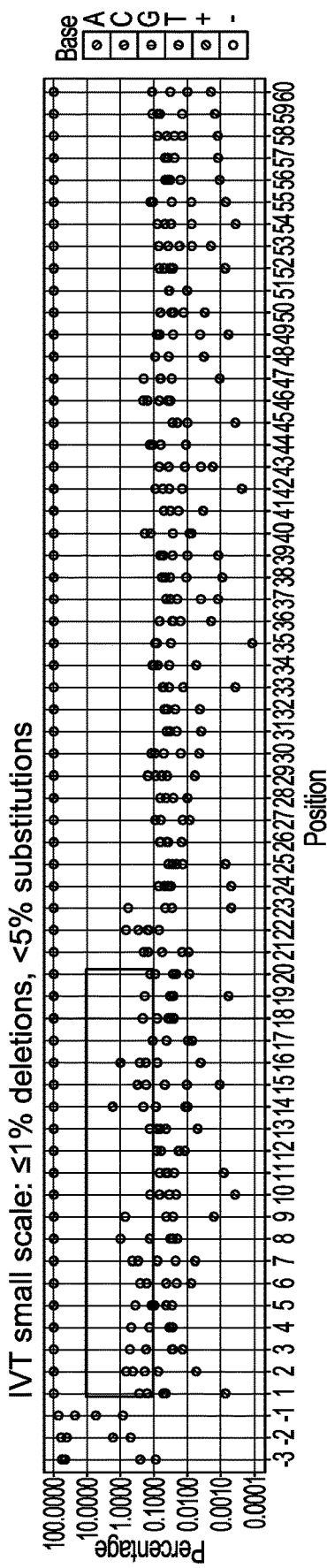
FIG. 7A shows plots depicting the frequency with which individual bases and length variances occur at each position from the 5' end of complementary DNAs (cDNAs) generated from the same gRNAs synthesized by in vitro transcription (IVT) as a small scale composition (top panel) and large scale production.
Figure 7A:
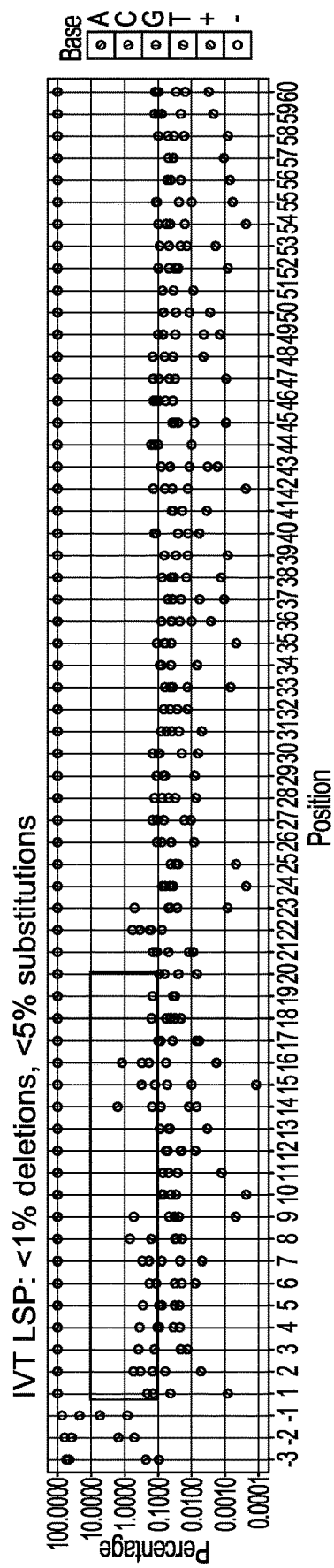
Figure 7B:
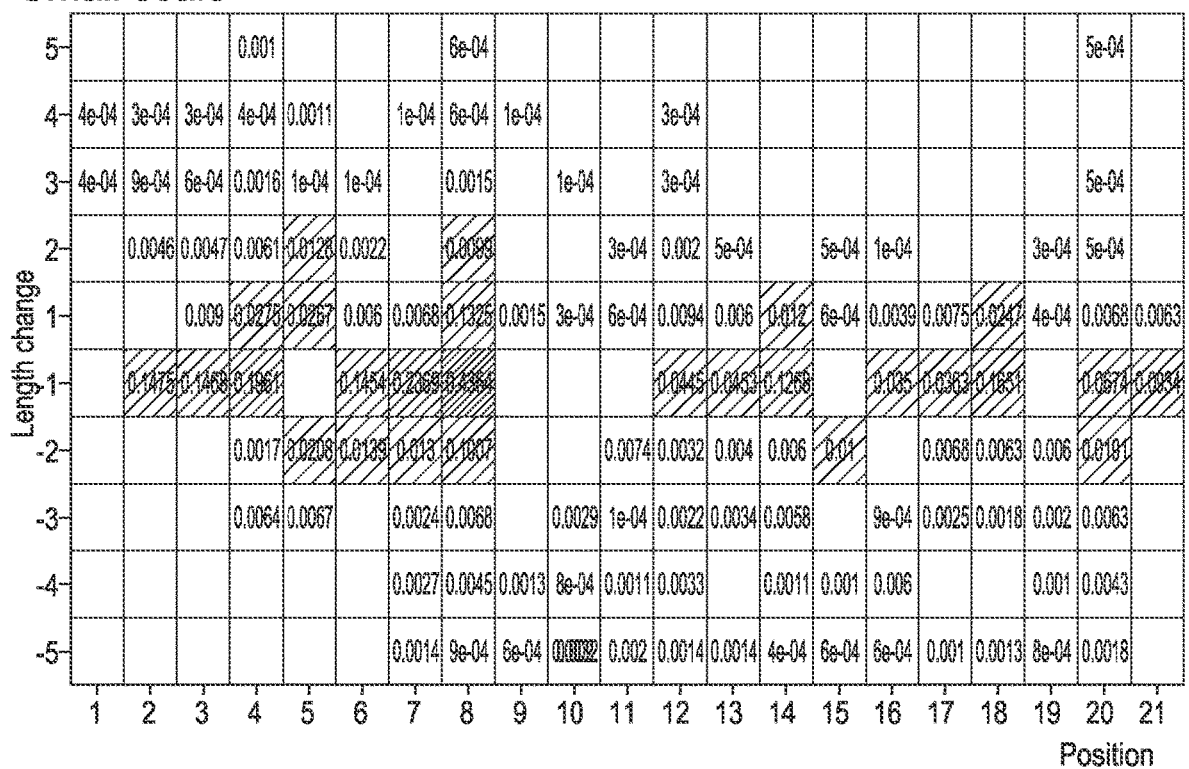
FIG. 7B includes graphs depicting internal sequence length variances at various position, relative to the reference sequence, for a small scale composition (top panel) and large scale production composition (lower panel) of the same gRNAs produced by IVT.
Figure 1:
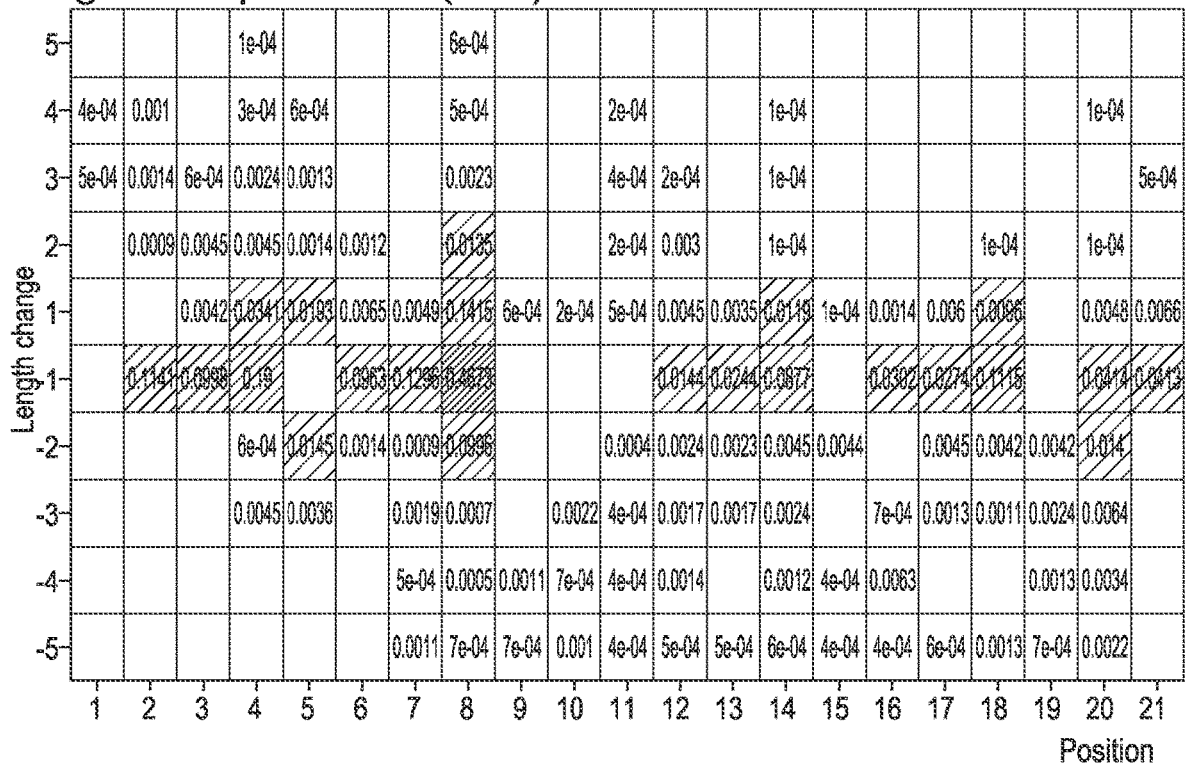

FIGS. 7A-7B depicts an in vitro case study that assessed lot-to-lot quality. In this case study, a gRNA was synthesized in vitro at small scale and large scale ("LSP"). Internal large scale production produced a lot of gRNA that edited less efficiently compared to the gRNA produced by the small scale lot. Expected spacer sequences were observed in both lots with similar indel/substitution profiles after using the provided methods described herein. Accordingly, the provided methods were able to show that the difference in editing efficiency between the lots were sequence independent.

Figure 8A:
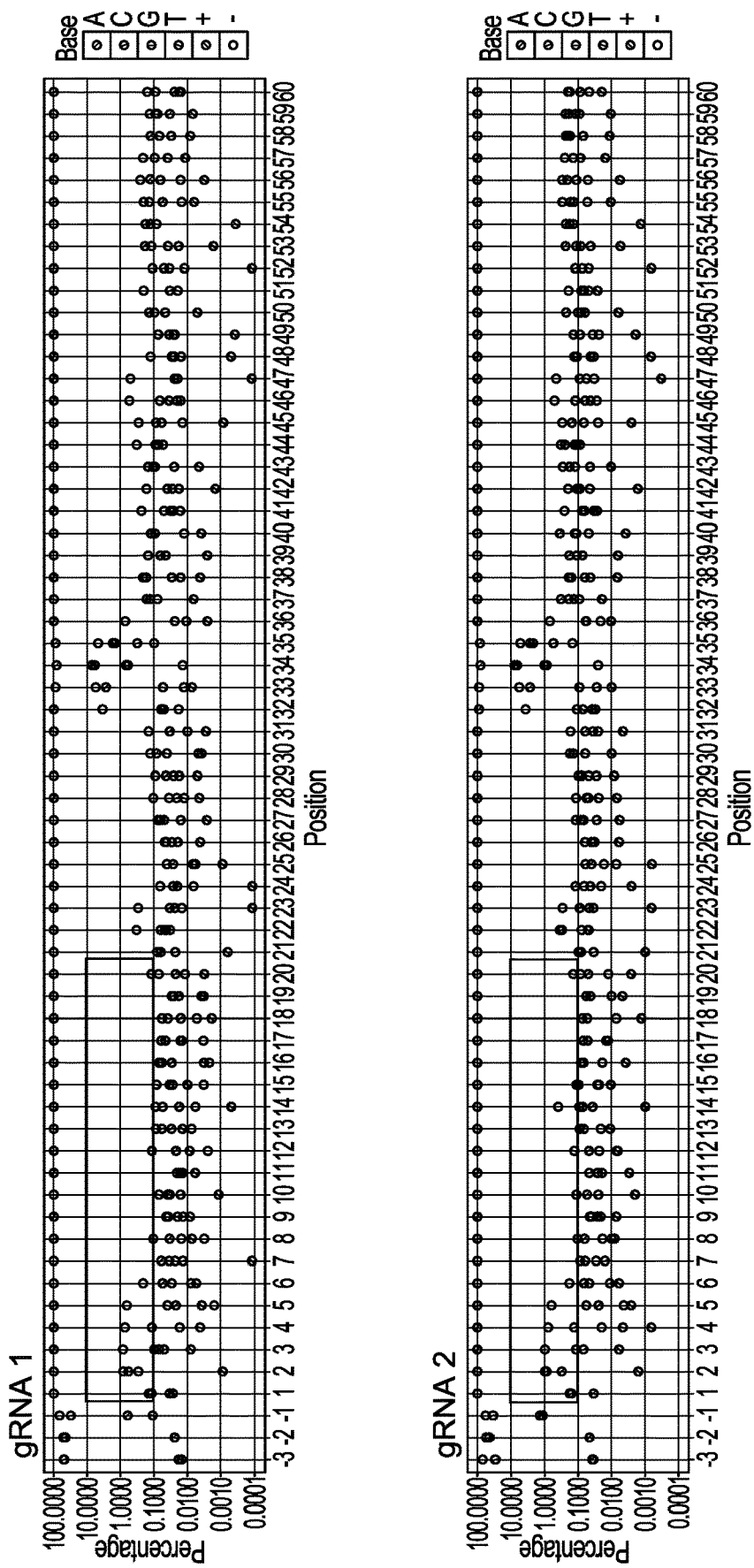
FIG. 8A shows plots depicting the frequency with which individual bases and length variances occur at each position corresponding to the 5' ends of gRNAs from the same synthetic gRNA lot. The plots were generated from two independent replicate analyses of the same synthetic lot.
Figure 8B:
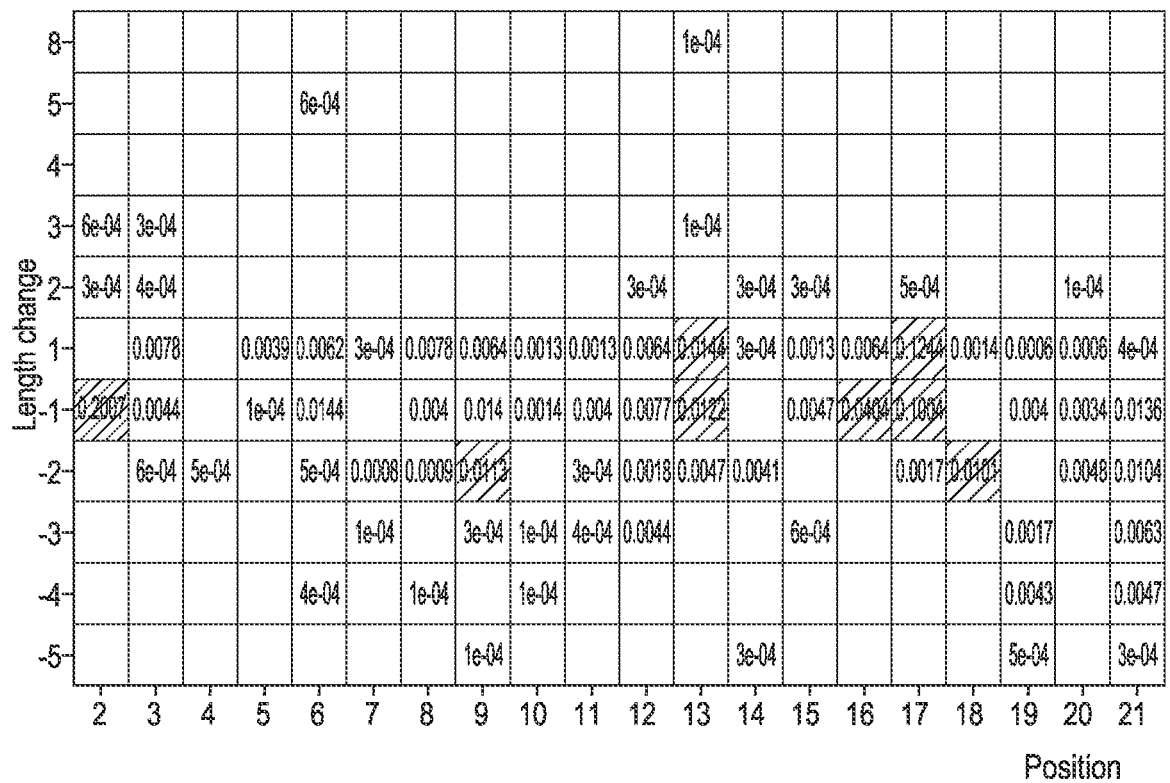
FIG. 8B depicts internal sequence length variances observed at the first 60 positions, from the 5' end of the gRNA, in the first (top panel) and second replicates (bottom panel).
Figure 1:
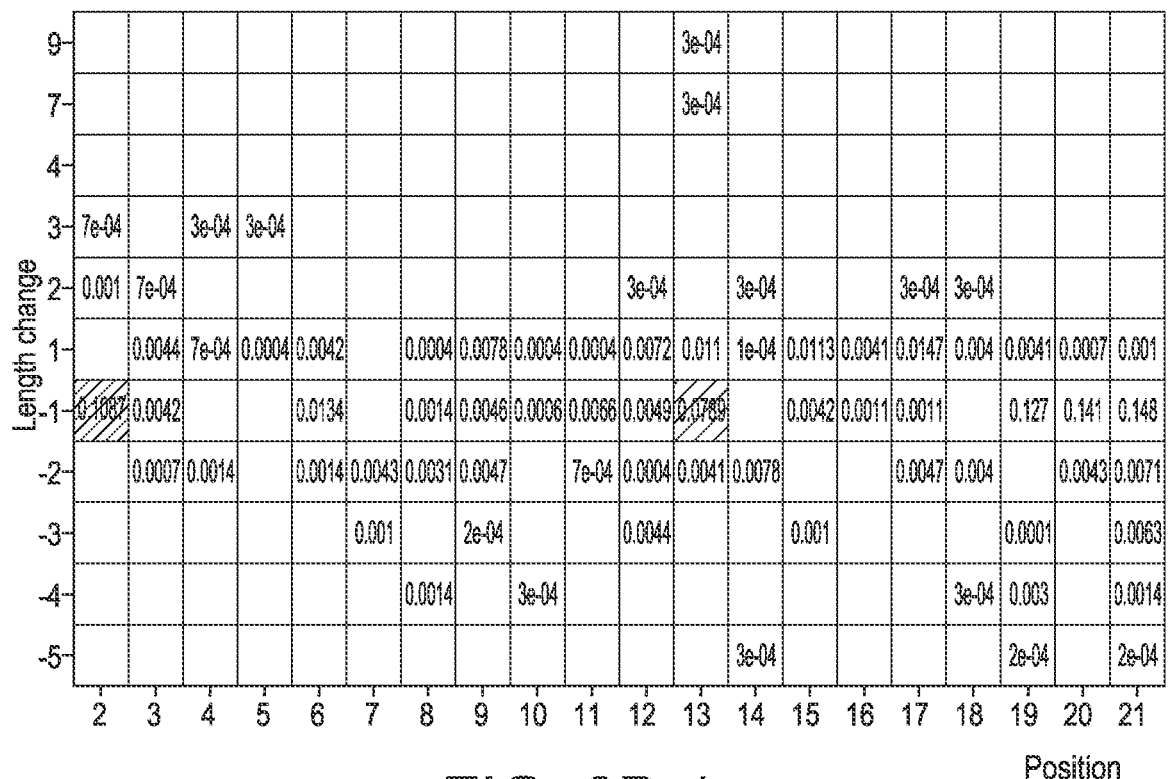

FIGS. 8A and 8B demonstrate that the assay was reproducible (i.e., the assay yielded consistent results across multiple replicates from the same base sample). FIGS. 8A-8B depict that the provided methods identified low inter-assay variability between experiments. Two gRNAs, gRNA 1 and gRNA 2, were prepared from a same lot of synthetic gRNA (urea) in two independent experiments. Profiles of frequency and length of mismatches were nearly indistinguishable across the two experiments.

Figure 9:
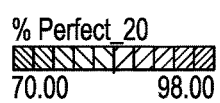
FIG. 9 shows a table depicting sequence fidelity of guides targeting a preselected site, where "% Perfect_20" is the percentage of sequence reads of guides whose first 20 bases map perfectly to the first 20 bases of the reference guide sequence. Some guides included modifications such as 5' cap variations (ARCA, InvG), 3' polyA tail, 2'-O-methylated (2'OMe) RNA bases, and phosphorothioate (PS) bonds in the backbone, as indicated.

FIG. 9 shows a table depicting sequence fidelity of guides targeting a predetermined site, where "% Perfect_20" was defined as the percentage of sequence reads whose first 20 bases map perfectly to the first 20 bases of the reference sequence. This "% Perfect_20" can be used as a metric of guide fidelity, for example, across multiple vendors, batches, formats, and modifications described herein (e.g., 5' cap variations (ARCA, InvG), 3' polyA tail, 2'-O-methylatated (2'OMe) RNA bases, and phosphorothioate (PS) bonds in the backbone).

Figure 11A:
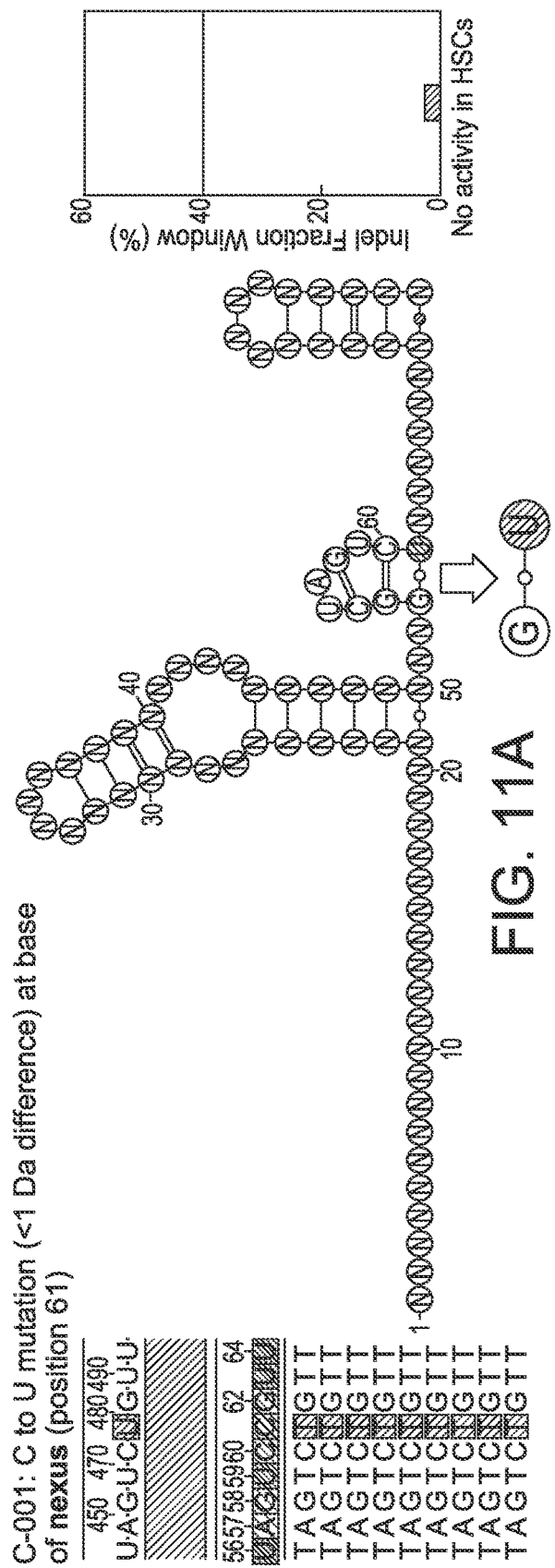
FIGS. 11A and 11B depict schematics of, and editing data from, guide RNAs that differ in the nucleotide at position 61 at the base of the *nexus* region. Using methods of the disclosure, guide "C-001" was found to include a mutated "U" at position 61, whereas guide "C-002" includes a "C" at position 61. The mutation at this position in C-001 resulted in loss of editing in cells that was rescued once the mutation was corrected and confirmed in batch C-002.
Figure 11B:
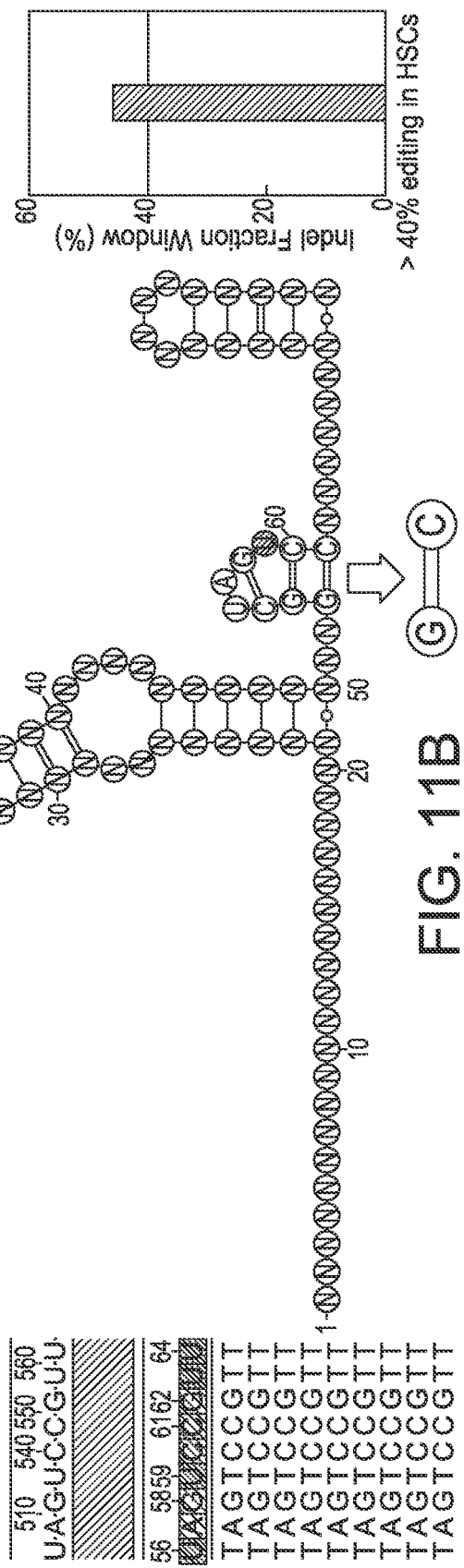

FIGS. 11A and 11B show data demonstrating the importance of the *nexus* region of the guide RNA on editing activity. "C-001" and "C-002" are separate oligonucleotide batches that have identical sequences except for one position (position 61) in the *nexus* region. A mutation at this position in C-001 (detected using the method described here) resulted in loss of editing in cells that was rescued once the mutation was corrected and confirmed in batch C-002.

Together, these data support the view that the systems and methods of the present disclosure can help to assess quality and purity of gRNA samples.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of assessing a sample of guide RNA molecules, comprising:
   (a) determining the nucleotide sequences of a plurality of guide RNA molecules of the sample, wherein the step of determining comprises combining:
      (i) the plurality of guide RNA molecules;
      (ii) one or more template switching oligonucleotides comprising a 3' hybridization domain and a sequence adapter;
      (iii) a retroviral reverse transcriptase; and
      (iv) dNTPs;
   (b) comparing the nucleotide sequences of the plurality of guide RNA molecules to a reference guide RNA sequence to identify truncation variants and/or sequence variants, relative to the reference guide RNA sequence;
   (c) determining a level of truncation variants comprising a truncation, relative to the reference guide RNA sequence;
   (d) determining a level of sequence variants comprising one or more of a nucleotide substitution, insertion or deletion, relative to the reference guide RNA sequence, within the 100 nucleotides proximate to a 5' end of the reference guide RNA sequence and/or within a bulge region of the reference guide RNA sequence and/or within a *nexus* region of the reference guide RNA sequence; and
   (e) for each sequence variant guide RNA molecule present at a level greater than or equal to 0.1%,
      (i) identifying the nucleotide sequence of the targeting domain of the sequence variant; and
      (ii) determining one or more potential off-target sites for the targeting domain of the sequence variant.

2. The method of claim 1, wherein the guide RNA molecules and the reference guide RNA sequence comprise a targeting domain within the first 30 nucleotides.

3. The method of claim 1, comprising determining the level of sequence variants comprising one or more of a nucleotide substitution, insertion or deletion within the *nexus* region, relative to the reference guide RNA sequence.

4. The method of claim 1, comprising determining the level of sequence variants comprising one or more of a nucleotide substitution, insertion or deletion within the bulge region, relative to the reference guide RNA sequence.

5. The method of claim 1, further comprising assigning a value to the sample of guide RNA molecules based on the determined level of truncation variants and/or sequence variants.

6. The method of claim 1, further comprising assigning a mismatch frequency to the sample of guide RNA molecules based on the determined level of truncation variants and/or sequence variants.

7. The method of claim 1,
   comprising combining (i)-(iv) in a reaction mixture under conditions sufficient to produce a plurality of product nucleic acids, each product nucleic acid comprising (i) a guide RNA molecule and (ii) the one or more template switching oligonucleotides, each hybridized to adjacent regions of a single product nucleic acid comprising a region polymerized from the dNTPs by the retroviral reverse transcriptase, wherein the region polymerized from the dNTPs comprises a domain that is complementary to and hybridized to the 5' end of the guide RNA molecule.

8. The method of claim 1, wherein the guide RNA molecules are non-polyadenylated, and the method further comprises polyadenylating the 3' ends of the non-polyadenylated guide RNA molecules.

9. The method of claim 7, wherein the 3' hybridization domain comprises a homo-trinucleotide.

10. The method of claim 9, wherein the homo-trinucleotide comprises guanine nucleotides.

11. The method of claim 9, wherein the method comprises combining:
    the plurality of guide RNA molecules; and
    a heterogeneous mixture of template switching oligonucleotides comprising a 3' hybridization domain and a sequence adapter and wherein the 3' hybridization domains comprise a partially degenerate sequence of guanine nucleotides and cytosine nucleotides (SSS).

12. The method of claim 9, wherein the one or more template switching oligonucleotides comprise a 5' domain comprising one or more isomers of guanine nucleotides or cytosine nucleotides.

13. The method of claim 9, wherein the one or more template switching oligonucleotides comprise a unique molecular identifier.

14. The method of claim 1, wherein the sequence adapter comprises a nucleic acid domain selected from the group consisting of a domain that specifically binds to a surface-attached sequencing oligonucleotide, a sequencing primer binding domain, a barcode domain, a barcode sequencing primer binding domain, a molecular identification domain, and a combination thereof.

15. The method of claim 13, wherein the identifying steps and/or determining steps comprise identifying the unique molecular identifier.

16. The method of claim 9, further comprising contacting a 3' region of the single product nucleic acid complementary to the one or more template switching oligonucleotides with a second strand primer configured to bind thereto under hybridization conditions.

17. The method of claim 9, further comprising contacting the guide RNA molecules with a first primer that primes the synthesis of the single product nucleic acid.

18. The method of claim 7, further comprising subjecting the single product nucleic acid to nucleic acid amplification conditions.

19. The method of claim 1, wherein the guide RNA molecules comprise a 5' modification.

* * * * *